United States Patent
Nolan

(10) Patent No.: US 11,400,111 B2
(45) Date of Patent: Aug. 2, 2022

(54) METHOD FOR PRODUCING GUM ARABIC ENCAPSULATED METAL NANOPARTICLES

(71) Applicant: Novus Research Group, LLC, Orem, UT (US)

(72) Inventor: Ryan P Nolan, Sycamore, IL (US)

(73) Assignee: Novis, Inc., Payson, UT (US)

( * ) Notice: Subject to any disclaimer, the term of this patent is extended or adjusted under 35 U.S.C. 154(b) by 0 days.

(21) Appl. No.: 16/206,487

(22) Filed: Nov. 30, 2018

(65) Prior Publication Data

US 2020/0171081 A1   Jun. 4, 2020

(51) Int. Cl.

| | |
|---|---|
| *A61K 9/51* | (2006.01) |
| *A61K 33/242* | (2019.01) |
| *A61K 33/38* | (2006.01) |
| *A61K 9/08* | (2006.01) |
| *A61K 9/06* | (2006.01) |
| *B82Y 5/00* | (2011.01) |

(52) U.S. Cl.
CPC ............. *A61K 33/242* (2019.01); *A61K 9/06* (2013.01); *A61K 9/08* (2013.01); *A61K 9/5176* (2013.01); *A61K 9/5192* (2013.01); *A61K 33/38* (2013.01); *B82Y 5/00* (2013.01)

(58) Field of Classification Search
CPC .......... A61K 9/06; A61K 9/08; A61K 9/5176; A61K 9/5192; A61K 33/242; A61K 33/38; B82Y 5/00
See application file for complete search history.

(56) References Cited

FOREIGN PATENT DOCUMENTS

| KR | 2005015195 A | * | 2/2005 | ............... C05D 9/00 |
| WO | WO-2017071949 A1 | * | 5/2017 | .......... B01J 13/0043 |

OTHER PUBLICATIONS

Lodeiro et al., Silver nanoparticles coated with natural polysaccharides as models to study AgNP aggregation kinetics using UV-Visible spectrophotometry upon discharge in complex environments, Jan. 1, 2016, Science of the Total Environment, vol. 539, pp. 7-16. (Year: 2016).*

El-Batal et al., Physiological Responses of Two Varieties of Common Bean (*Phaseolus vulgaris* L.) to Foliar Application of Silver Nanoparticles, 2016, Nanomater Nanotechnol, vol. 6 iss. 13, pp. 1-16 (Year: 2016).*

* cited by examiner

*Primary Examiner* — Ali Soroush

(74) *Attorney, Agent, or Firm* — Frederic M. Douglas

(57) ABSTRACT

The present invention may comprise stabilized metal nanoparticles that are stabilized with material from gum arabic. The nanoparticles of the invention may be manufactured with an environmentally friendly method for fabricating biocompatible stabilized metal nanoparticles. The coated metal nanoparticles may be introduced in vivo to conduct therapy for humans or animals.

7 Claims, 34 Drawing Sheets

METHOD FOR PRODUCING GUM ARABIC ENCAPSULATED METAL NANOPARTICLES

BACKGROUND OF THE INVENTION

The present invention relates generally to dental and gingival preventative treatments by using novel methods for synthesizing metal nanoparticles. More specifically, the present invention relates to methods for preventing dental decay, altering the composition of dental plaque to reduce pathogenic effects, minimizing pain, swelling, and infection before, and subsequent to, dental surgery and dental procedures.

Silver salts are anti-microbial, as well as silver particles of micro size (one dimension less than or equal to $1\times10^{-6}$ meters) or nano size (one dimension less than or equal to $1\times10^{-9}$ meters). Silver particles in a colloid are formed from dispersing the silver particles within another substance, often water. Metal salts and metal nanoparticles may behave similarly, such as gold, platinum, iron, copper, other transition metals, or salts thereof. A sol is when a colloid or colloidal suspension comprises particles dispersed within a liquid. When the sol comprises, particles dispersed in liquid water, the sol is a hydrosol.

The usefulness of hydrosols of metal nanoparticles comes from the ability to kill microorganisms and prevent multiplication of microorganisms to prevent decay, alter plaque, and to reduce pain, swelling, and infections relating to dental surgery and procedures.

Most of the known synthetic methods for the production of metal nanoparticles rely on the use of organic solvents, such as acetone, chloroform, dimethylsulfoxide (DMSO), and the like, and toxic reducing agents, such as hydrazine, dimethylformamide (DMF), sodium borohydride, and so on, in addition to requiring additional separate stabilizing agents. Customarily such chemicals used are toxic and pose potential environmental and biological risks. Additionally, such substances are costly and are therefore not favored for industrial applications.

These methods have several additional drawbacks, including a tendency to not retain stability in the presence of a high concentration of calcium salt, instability at high temperatures, and susceptibility to breakdown outside of narrow pH ranges.

Thus, it would be advantageous to have a range of methods that retain stability in the presence of a high concentration of calcium salt, maintain stability at high temperatures, and produce product that is sustainable over a wide pH range.

As will be seen more fully below, the present invention is substantially different in structure, process, and approach from that of the prior gum arabic coating systems for metal nanoparticles.

SUMMARY OF THE INVENTION

Facile green synthesis method for the production of high biocompatibility, high stability noble, semi-noble and base colloidal metal nanoparticles in the presence of high salt concentrations (such as high calcium salt concentrations), high heat applications, and under a wide pH range.

In one aspect of the present invention, a kit for treating patients with gum arabic encapsulated metal nanoparticles, may comprise; metal nanoparticles directly coated with gum arabic, and an aqueous solution of the gum arabic, wherein the gum arabic is present at least at 12 weight percent in a base solution prepared.

In another aspect of the present invention, metal nanoparticles stabilized with a material coating may comprise gum arabic in an aqueous solution wherein the aqueous solution contains at least 12 weight percent gum arabic, wherein the metal nanoparticles comprise of metal cores, and wherein the metal cores are in the size range of about 9 nm to about 16 nm, often from about 5 nm to about 10 nm.

In yet another aspect of the present invention, a method for reducing pain, swelling, and infection resulting from dental procedures may comprise the steps of; making an incision into, or a wound in, gingival or dental tissues within the mouth of a patient, applying a gel containing a silver nanoparticle hydrosol, or other transition metal nanoparticle hydrosol, to the incision, bone graft, or the wound, and rinsing the mouth periodically with an aqueous rinse containing a silver metal nanoparticle hydrosol solution to reduce the bacterial load thereby reducing pain and swelling or infection resulting from dental procedures, wherein a base (concentrated) synthesized aqueous nanoparticle solution contains at least 12 weight percent gum arabic. The rinses made may be diluted from this base concentrated solution as each situation requires.

These and other aspects, objects, features, and advantages of the present invention are specifically set forth in or will become apparent from, the following detailed description of an exemplary embodiment of the invention when read in conjunction with the accompanying drawings.

DETAILED DESCRIPTION OF THE INVENTION

Figure 1:
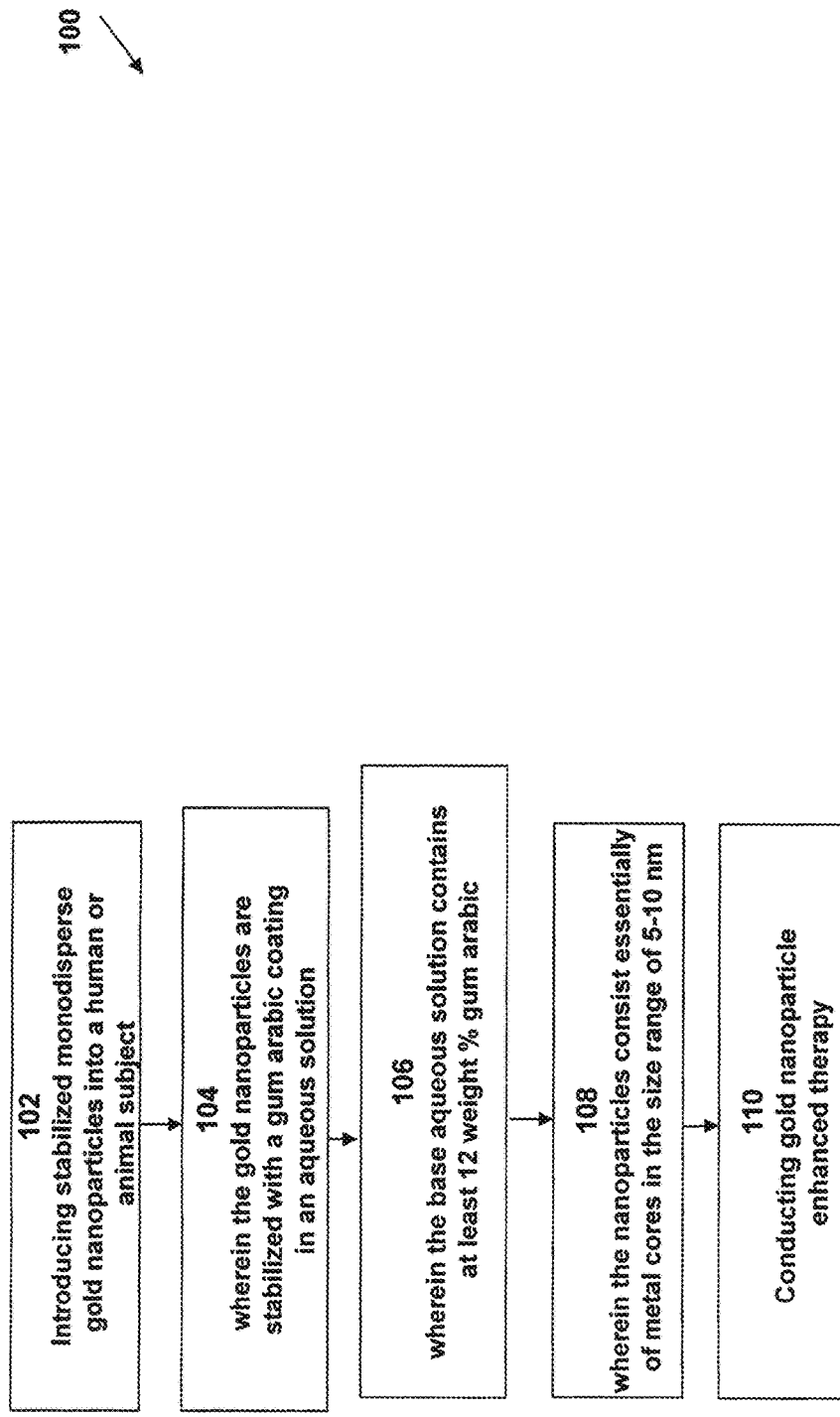
FIG. 1 is a flowchart showing a method of therapy comprising introducing stabilized gold nanoparticles into a human or animal subject and conducting gold nanoparticle enhanced therapy, according to an embodiment of the present invention.
Figure 2:
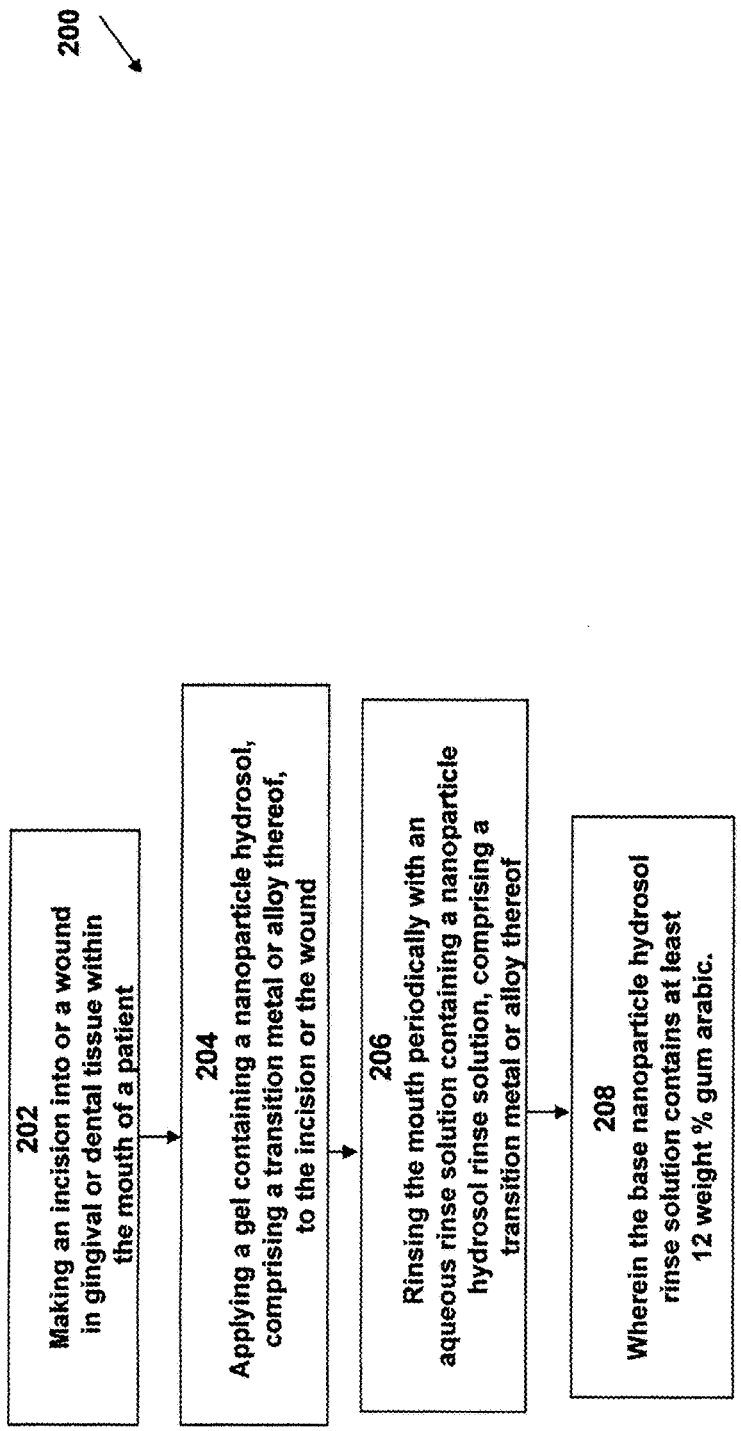
FIG. 2 is a flowchart showing a method for reducing pain, swelling, and infection resulting from dental procedures, according to another embodiment of the present invention.
Figure 3:
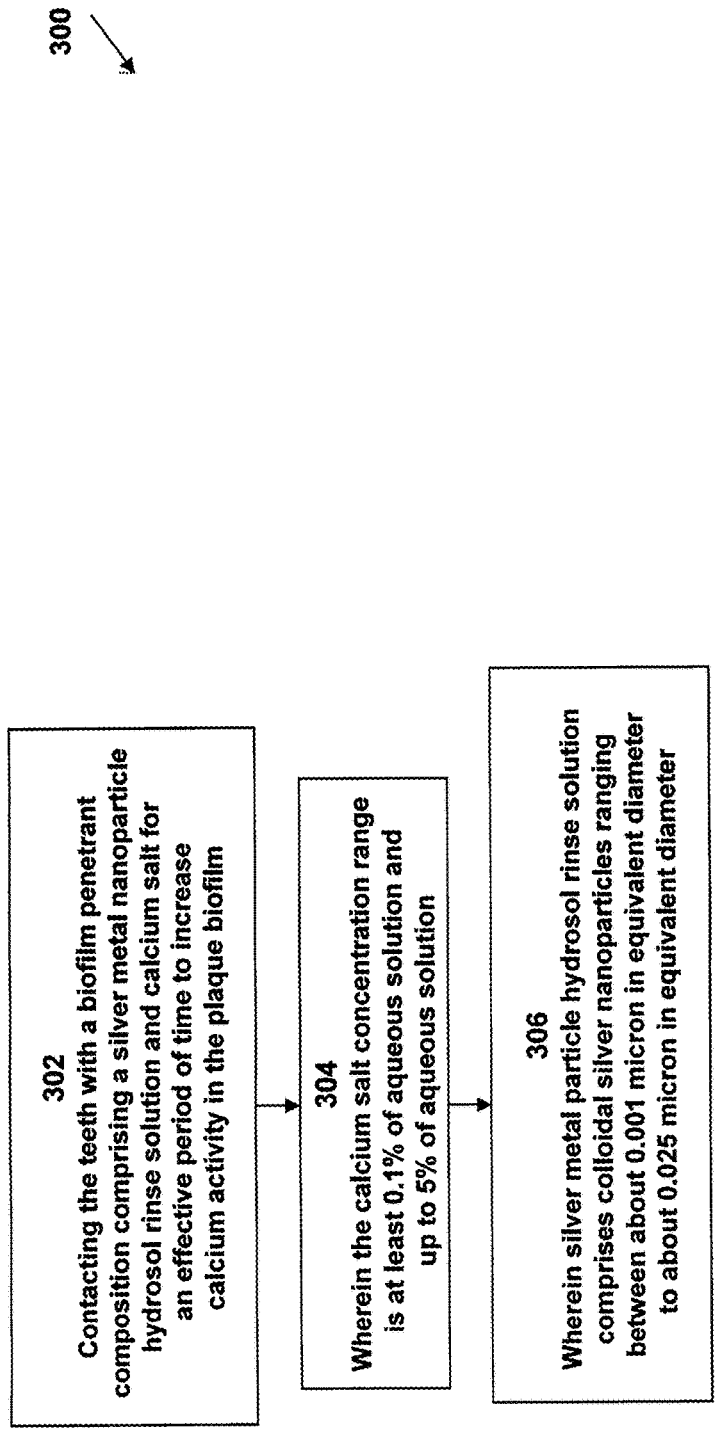
FIG. 3 is a flowchart showing a method for inhibiting and preventing dental caries and promoting calcium exchange, according to yet another embodiment of the present invention.

The following detailed description is of the best currently contemplated modes of carrying out the invention. The description is not to be taken in a limiting sense but is made merely for the purpose of illustrating the general principles of the invention, since the scope of the invention is best defined by the appended claims.

Although the inventions are often referred to herein as kits, apparatus, solutions, and methods for dental or gingival procedures or surgery, it is understood that such description is not limiting, such that the technology in this invention may be applied in numerous other products and methods, including but not limited to body imaging contrast systems, medical procedures, chemical or biological detectors, drug delivery systems, cancer treatments, wound treatments, and other methods using coated metal nanoparticles. In general, the order of the steps of disclosed methods may be altered within the scope of the invention. The metal nanoparticles produced by the methods disclosed herein also may have antibacterial properties.

The metal nanoparticles may be comprised of metals and/or metal oxides, such as Au, Ag, Pd, Pt, Rh, Ir, Cu, Co, Ni, Fe, Zn, or other suitable transition metals, or other suitable oxides. Sometimes metals may be known as "Noble metals" or "Semi-Noble metals." Examples of Noble metals are gold (Au), platinum (Pt), ruthenium (Ru), rhodium (Rh), palladium (Pd), osmium (Os), and iridium (Ir). The base metals include iron (Fe), cobalt (Co), nickel (Ni), copper (Cu), aluminum (Al), and tungsten (W). Silver (Ag) is often also considered a semi-noble metal. Many useful solutions are synthesized wherein the metal nanoparticles comprise transition metals including, but not limited to, iron, tungsten, nickel, ruthenium, rhodium, osmium, iridium, palladium, platinum, copper, gold, silver, alloys thereof, and mixtures thereof.

Many common methods for preparing metal nanoparticles result in poor stability for the final product and an even lower stability when diluted with water, which is customary for proper use. Cation and anion contaminants from salts present a significant deterrent to diluted product stability, resulting often in agglomeration of nanoparticles or dissolution in the form of silver ions which may further react unfavorably. When a quantity of metal nanoparticles is mostly not agglomerated and show a tighter size range (nm), one term often used describes the nanoparticles as more "monodisperse."

Prior methods have used gums, such as gum arabic or other capping agents to encapsulate the metal nanoparticles. Due to low ratios of gum to solution (low weight percentage of gum to metal salt in the synthesized base solution) in the prior processes, the coatings by the capping agent are easily destabilized, especially in the presence of ionic contaminants, such as +2 cations (e.g., $Ca^{+2}$) and common−1 anions such as chloride. Calcium cations may attach to nanoparticle surfaces, competing with the gum capping agent for surface adherence. The calcium cations and chloride anions, as one example, may also destabilize the encapsulated surfaces of the nanoparticles resulting in agglomeration and dissolution into useless or less useful products, especially when biological applications are concerned.

In various oral environments, calcium ion concentrations tend to be high while previous methods of gum arabic coating of metal nanoparticles provide low stability, fewer desirable small particles, and excessive non-desirable agglomeration especially in the presence of calcium. Previous art attempts at synthesizing metal nanoparticles show little to no stability in oral environments where ionic strength (where a key contributor to ionic strength is high levels of calcium) is high, and prior art synthesized metal nanoparticles would degrade quickly. An inventor frequently attempted gum arabic encapsulation of metal nanoparticles at customary weight percentages (e.g., 1:1 weight percent ratio of metal salt to gum) in aqueous solution and observed rapid degradation in the presence of calcium chloride. These unsatisfactory results happened for gold nanoparticles and silver nanoparticles. The methods of encapsulated metal nanoparticle synthesis described herein are "greener" or "bio-friendly" reaction methods than prior methods such that less energy input and avoidance of using strong amines, borohydrides, or other strong reducing agents drive the methods to promote a more complete reaction.

The inventors have found that customarily low-weight percentages of gum arabic in aqueous solution offer poor results when attempting to coat metal nanoparticles with gums and exposing diluted base solutions to high salt contaminant concentrations, such as contamination by sodium chloride or calcium chloride. Synthesized products are referred to as the "base" concentrated solutions, comprising varying levels of gum Arabic weight percentages. Using heavy loading of gum arabic in aqueous solution, within certain ranges, greatly improves nanoparticle encapsulation for beneficial uses in industry, research, medical treatments, dental treatments, and agriculture.

The methods described herein for coating and encapsulation of metal nanoparticles with highly concentrated gum arabic aqueous solution further provide results prolonging shelf life over prior methods. Others have tried methods to improve shelf life using lyophilization, wherein silver or gold nanoparticles are flash frozen with liquid nitrogen, vacuum distilled, and made into a powder form. The powder may later be reconstituted with deionized or distilled water.

Some aspects of synthesizing metal nanoparticles can optimally differ depending upon the type of metal used. The inventors discovered that superior results were obtained when synthesizing silver nanoparticles with 15 weight percent gum arabic and using instead 7.5 weight percent gum arabic when synthesizing gold nanoparticles. For processes intended for later powder reconstitution, superior results were obtained for silver nanoparticles synthesized with 15 weight percent gum arabic. For gold nanoparticles intended for later reconstitution, 15 weight percent gum arabic provided superior results over the prior known methods.

A method of synthesizing metal nanoparticles may comprise using a soluble metal salt, gum arabic, sodium hydroxide, and distilled or deionized water. One embodiment for synthesizing silver nanoparticles may comprise using silver nitrate, while other stable silver salts may be used. Metal salts ranging from 0.1 weight % to 10 weight %, often about 0.5 weight %, may be used.

The gum arabic should be pure and devoid of preservatives or carbohydrate enhancers. The gum arabic concentration may be 10 weight % or higher, with an upper range often used as high as 30-35 weight %. Often, a useful range between about 5 weight % to about 20 weight % of gum arabic for most metal particles. The ratio of weight % gum arabic to weight % silver salt is another indicator of stability. This may be noted in the synthesis table whereby ratios are compared. Previous methods (before this application) used much lower concentrations of gum arabic while requiring strong amine or borohydrate reducing agents to ensure additional reduction for the formation of stable nanoparticles. Here, unexpected experimental results lead to these new methods to increase the gum arabic content to around 15 weight %, which allows the gum arabic to act as a reduction agent and a steric hindrance (stabilizing) agent to avoid such harsh reducing agents such as strong amines or borohydrates. The new methods provide an end product that is stable in the presence of calcium salts, heat, or pH effects, especially when diluted in media contaminated with many ions (high ionic strength) and osmolytes. Prior methods also do not ensure complete reaction or surface saturation of particles to ensure increased stability in contaminated media, as is experienced with the new methods described herein.

Particle stability is maximized in the presence of salts, such as calcium chloride, at 15 weight % gum arabic content, while staying satisfactory at about 10 weight % but not improving greatly past about 15-20 weight %. Often 12 weight % gum arabic content serves to maximize the qualities of the end product while limiting excessive costs of excessive gum arabic ingredient. In other words, a balance between effectiveness and costs may be found at around 12 weight % gum arabic content when synthesizing gum-capped metal nanoparticles.

Sodium hydroxide may be used at concentrations ranging from about 0.1 weight % to about 3 weight %. Often, the concentration of 1 weight % (0.25 M) may be used to increase reaction pH to between 10-12 to assist in accelerating the reaction from oxidation of the metal in situ. Overall particle distribution variations can be reduced by dissolving the sodium hydroxide in distilled or deionized water before adding to the reaction. Pre-dissolving the sodium hydroxide makes the end product, gum-capped metal nanoparticles, monodisperse (less polydisperse) and provides an end product with higher uniformity than previous methods.

Using distilled or deionized water helps to lower ionic activity before adding ingredients fed to the reaction, keeping low the formation of byproducts and keeping high the stability of the end product.

The size ranges of the end product gum-capped metal nanoparticles may vary between 15-35%, often varying less than 30%, ranging in size between about 0.1 nm to about 50 nm, often within about 5 nm to about 10 nm in ideal diameter size.

These new methods avoid the need for heat input, or use of a centrifuge or other devices, and instead react at room temperature while many prior methods needed to be heated to drive the reaction to completion.

The desirability of the end product, gum arabic capped metal nanoparticles, may be analyzed by measuring the absorbance lambda, A, which may be between about 400 nm to about 420 nm for silver nanoparticles, between about 510 nm to about 540 nm for gold nanoparticles, and in other ranges for other metals.

Desirable results may be achieved from a reaction time of about 20 minutes, in the absence of light in a covered area. Continuous agitation, such as with a magnetic stir bar, may help for the duration of the reaction.

In one exemplary reaction, with many steps interchangeable in sequence, the reaction vessel may contain from about 1 weight % to about 83.5 weight % distilled water with gum arabic added in a ratio of 15 weight % or greater and mixed with a stir bar until dissolved. 0.5 weight % metal salt may follow in from about 0.5 weight % to about 10 weight % (depending upon weight % of gum arabic used). After the gum is mixed and integrated into the colloid or colloidal suspension, a sodium hydroxide solution may be added while the reaction is mixing.

The sodium hydroxide solution may comprise from about 1 weight % to about 15 weight % distilled water and often about 1 weight % sodium hydroxide.

When setting a solution of compounds for reactions more likely to near completion, a useful range for a silver salt initial input of 0.5 weight %, will form about 1 mg/mL to about 5 mg/mL of nano silver particles, often 3.175 mg/mL.

The reaction time may take from about 12 hours to about 24 hours, at room temperature, in a covered area without light exposure.

In another embodiment of the methods, from about 1 weight % to about 83.5 weight % of distilled water may be added to a reaction vessel, followed by the gum arabic in a ratio of 15 weight % or greater of the final product and mixing with a stir bar until the gum arabic is dissolved. A silver salt, such as $AgNO_3$, in 0.5 weight % concentration, may be added to distilled water from about 1 weight % to about 10 weight % distilled water. The sodium hydroxide should be dissolved in deionized water and the resulting sodium hydroxide solution should be added last to the reaction vessel. The solution which contains the remaining 1-15 weight % distilled water and sodium hydroxide (1 of overall weight %) may be added while the reaction mixes to ensure the complete formation of the final product. Pre-dissolving the ingredients in water can ensure a more evenly distributed nucleation of the particles.

The methods of encapsulating metal nanoparticles described herein may be used to encapsulate various types of transition metal nanoparticles as the methods described herein provide superior reduction capabilities and stabilization properties. Determining the respective amounts of gum arabic, water, and other components for each specific metal nanoparticle may be predicted using a density-based approach. For transition metals between density (10.5-19.3 $g/cm^3$):

Gum Arabic(weight %)required=((0.15)+(Density of transition metal $g/cm^3$–10.5 $g/cm^3$)(−0.0085034014))*100%

If the gum encapsulated metal nanoparticles are heated after formation, the nanoparticles may form a solid crystalline mass, which later may be re-dispersible when added to water. To promote consistent size and stability upon reconstitution, however, freeze drying the product requires lyophilization, which is a superior process for fabricating a stable re-dispersable nanopowder from a base solution.

Lyophilization, also called "freeze-drying" or "cryodesiccation," involves freezing the product and then removing water from the product under a vacuum.

In lyophilization, the ice formed from freezing changes from solid to vapor without traversing the liquid phase. The end product, gum arabic capped metal nanoparticles may be lyophilized for longer shelf life. The results have been desirable from lyophilizing the end product manufactured according to the methods described herein.

The lyophilized product may be reconstituted at various levels of gum arabic, such as 15 weight % for gold nanoparticles and also 15 weight % for silver nanoparticles, which are superior to lesser concentrations of 1.0 weight %, 2.5 weight %, 5.0 weight %, 7.5 weight %, or 10.0 weight %.

The gum-encapsulated metal nanoparticles produced by the methods described herein have beneficial characteristics, such as high heat resistance, high light resistance, resistance to chemical agglomeration, resistance to physical agglomeration, high stability in high ionic strength solutions and high osmolyte concentrations. The product, gum-capped metal nanoparticles retain these properties, even when diluted to from about 5 parts per million to about 20 parts per million. The product may be stable, kinetically and sterically, for about 1 year to about 5 years.

The product is stable in the presence of various osmolytes. This characteristic is useful in dental applications as many osmolytes are used for dental products, such as xylitol, mannitol, sorbitol, erythritol, and other sugars or sugar alcohols.

The product produced by the methods herein exhibit stability in the presence of high salt concentrations, especially in the presence of 2+ cation salts, high levels of chloride (−1) as well as osmolyte concentrations greater than, or equal to, about 25%, for which an example involving xylitol is provided.

Synthesized silver nanoparticles may be useful for anti-caries benefits at a concentration between about 5 ppm to about 30 ppm, often from about 10 ppm to about 15 ppm via increasing active calcium ion activity or active fluoride activity (among other beneficial salts, minerals, enzymes, and proteins) into the plaque fluid of the plaque biofilm.

Metal nanoparticles synthesized and encapsulated as described in the methods herein are stable in the presence of fluoride salts, such as synthesized silver nanoparticles. The metal nanoparticle gum arabic encapsulated products described herein are also stable in media comprising sugar alcohols (for example, xylitol) and calcium salts at high levels. In one formulation, oral care solutions containing 25% xylitol with calcium ions with gold or silver nanoparticles with gum arabic coatings have a long shelf life not observed previously with other known methods of synthesizing metal nanoparticles.

The synthesized silver nanoparticles may be used for anticaries benefits in dentifrices at a concentration between about 5 ppm to about 30 ppm, often from about 10 ppm to about 20 ppm by increasing active calcium, acetate, phosphate, bicarbonates, or other pH-neutralizing agents' activity in the plaque fluid of the plaque biofilm. In another embodiment the silver nanoparticles may be used via deposition and incorporation into tooth structures, increasing the charge density of the tooth mineral surface which may deter and prevent damage from acid attacks produced by bacteria.

The metal nanoparticles may be deposited via a pulsed laser treatment from a ND YAG, Er, Cr, YSGG, Argon, Diode, or ER YAG laser over via laser ion doping, thereby improving the incorporation of these nanoparticles into tooth surfaces.

Various embodiments of the methods are described below via experiments and experimental results that illustrate various aspects of kits, metal nanoparticles, and methods, including the benefits and advantages achieved through some exemplary methods. Those knowledgeable and familiar in the relevant art will appreciate that results from the experiments may translate to other environments or situations.

Experiments have demonstrated the unexpected result that a certain range of gum arabic concentrations for synthesizing gum-encapsulated metal nanoparticles are particularly effective in producing end products that retain stability in the presence of a high concentration of calcium salt, maintain stability at high temperatures, and are sustainable over a wide pH range.

EXPERIMENTAL

Figure 4:
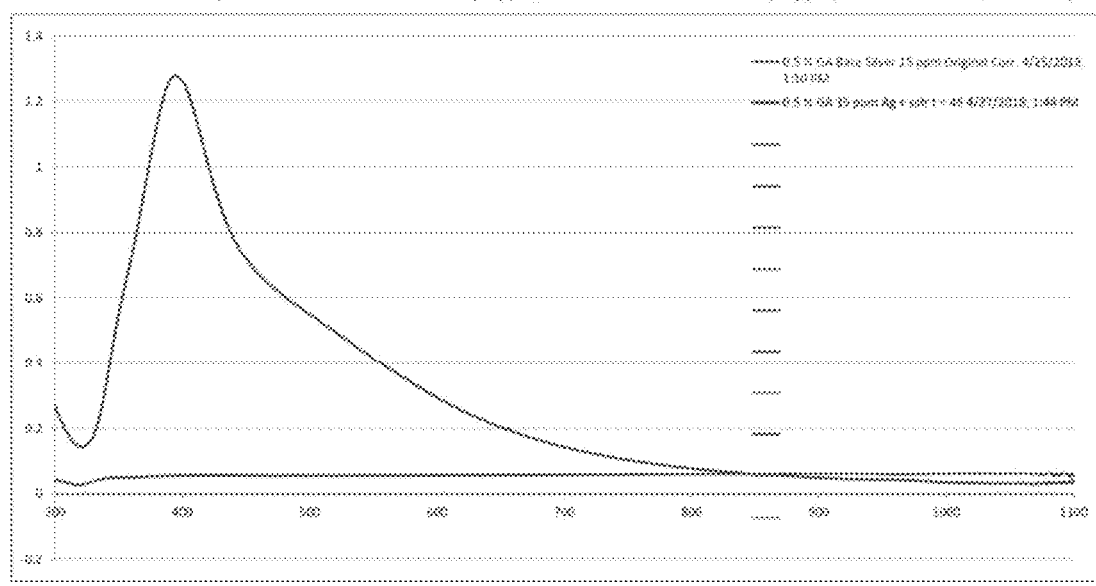
FIGS. 4-65 show experimental results for various gum arabic concentrations when preparing silver nanoparticles encapsulated in gum arabic.
Figure 65:
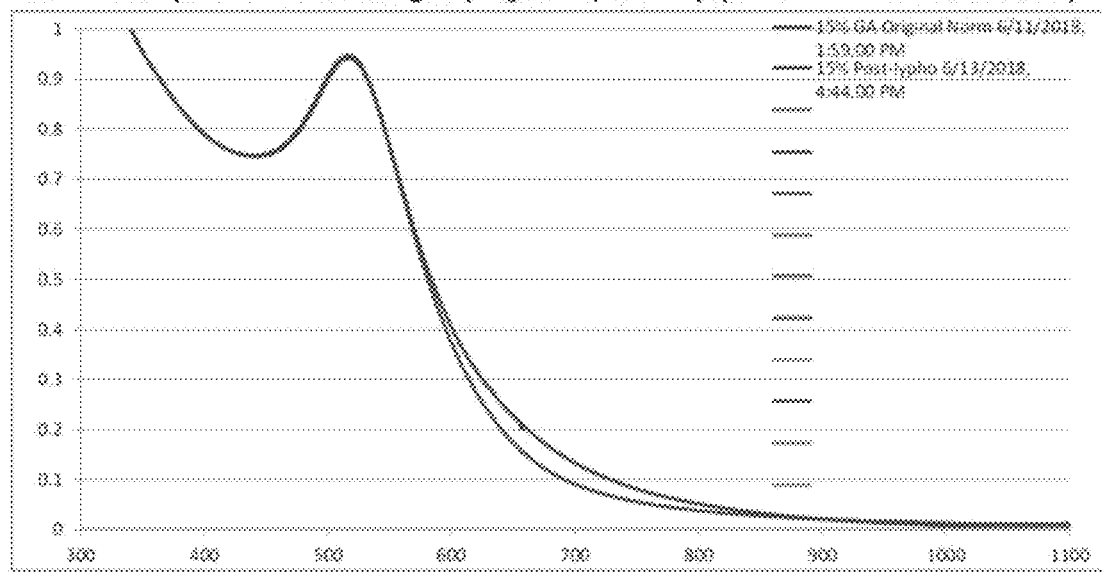

FIGS. 4-65 and tables 1-3 contain synthesis information and show experimental results for various gum arabic concentrations when preparing silver nanoparticles encapsulated in gum arabic. The plots in FIGS. 4-65 show absorbance (Y-axis) vs. wavelength (X-axis).

Synthesis of Gum Arabic Encapsulated Silver Nanoparticles—0.5% GA 0.5 weight % (0.25 g/50 mL solution) of gum arabic (GA) is dissolved in de-ionized (DI) water (or distilled water) at room temperature with continuous stirring with a magnetic stirring bar. Silver salt is then added to the GA solution as 0.5 weight % (0.25 g AgNO$_3$/50 mL solution), followed by a sodium hydroxide solution 1.0 weight % of NaOH (0.5 g/50 mL solution), often added to ~5 mL-10 mL of deionized water while being continuously stirred with a magnetic stirring bar.

After about 24 hours of stirring, without heating, the product formed, GAAgNPs (Gum Arabic-silver-NanoParticles), may be analyzed by optical absorbance measurements, with a spectrophotometer, such as the Agilent 8453 Spectrophotometer sold by Agilent Technologies of 5301 Stevens Creek Blvd., Santa Clara, Calif., U.S.A. 95051.

Representative proportions are provided in Table 1.

TABLE 1

Synthesized Base Nanosilver Gum Arabic Nanoparticles GAAgNPs (Experimenta Samples):

| Sample: | Silver Salt (AgNO$_3$) (Wt %) | Gum Arabic (Wt %) | Ratio of Gum Wt %:Salt Wt % | Accelerator (NaOH Wt %) |
|---|---|---|---|---|
| GA-BASE (0.5) | 0.5% (0.25 g/50 ml.) | 0.5% (0.25 g/50 mL) | 1:1 | 1% (0.5 g/50 mL) |
| GA-BASE (1) | 0.5% | 1% (0.5 g/50 mL) | 2:1 | 1% |
| GA-BASE (2.5) | 0.5% | 2.5% (1.25 g/50 mL) | 5:1 | 1% |
| GA-BASE (5) | 0.5% | 5% (2.5 g/50 mL) | 10:1 | 1% |
| GA-BASE (7.5) | 0.5% | 7.5% (3.75 g/50 mL) | 15:1 | 1% |
| GA-BASE (10) | 0.5% | 10% (5 g/50 mL) | 20:1 | 1% |
| GA-BASE (12.5) | 0.5% | 12.5% (6.25 g/50 mL) | 25:1 | 1% |
| GA-BASE (15) | 0.5% | 15% (7.5 g/50 mL) | 30:1 | 1% |

Figure 5:
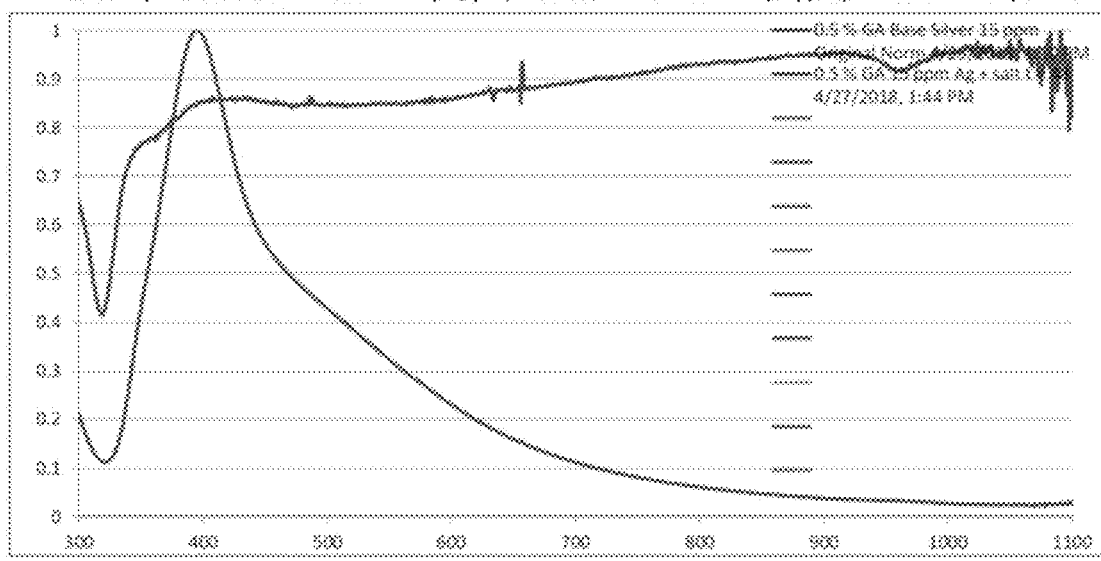

The results are plotted in FIGS. 4 and 5, for 0.5 weight % GA nanosilver (15 ppm) and for 0.5 weight % GA nanosilver (15 ppm) with the addition of 1.0 weight % calcium chloride (CaCl$_2$)). As shown in FIGS. 4 and 5, the results without CaCl$_2$) have a peak of somewhat satisfactory results while the plot for the process in the presence of the CaCl$_2$) shows rather poor, unsatisfactory results in the form of a normalized and dilution corrected charts (FIGS. 4 and 5).

Representative proportions are provided in Table 2.

TABLE 2

NANOSILVER EXPERIMENTAL SAMPLES
for Calcium salt Stability study:

| Sample:<br>(GAAgNP samples derived<br>from synthesis from table 1) | Nanosilver(15 ppm) + Deionized<br>H2O + 1 Wt % CaCl$_2$:<br>EXPERIMENTAL SALT TRIAL |
|---|---|
| GA-CAL(0.5) | 0.5% GA Sample |
| GA-CAL(1) | 1% GA Sample |
| GA-CAL(2.5) | 2.5% GA Sample |
| GA-CAL(5) | 5% GA Sample |
| GA-CAL(7.5) | 7.5% GA Sample |
| GA-CAL-(10) | 10% GA Sample |
| GA-CAL-(12.5) | 12.5% GA Sample |
| GA-CAL-(15) | 15% GA Sample |

Synthesis of Gum Arabic Encapsulated Silver
Nanoparticles—1.0% GA 1.0 weight % of gum arabic (GA) (0.5 g/50 mL solution) is dissolved in de-ionized (DI) water (or distilled water) at room temperature with continuous stirring with a magnetic stirring bar. Silver salt is then added to the GA solution as 0.5 weight % (0.25 g AgNO$_3$/50 mL solution), followed by a sodium hydroxide solution 1 weight % of NaOH (0.5 g/50 mL solution, often added to ~5 mL-10 mL of deionized water first) while being continuously stirred with a magnetic stirring bar.

After 24 hours of stirring, without heating, the product formed, GAAgNPs, are analyzed by optical absorbance measurements.

Figure 6:
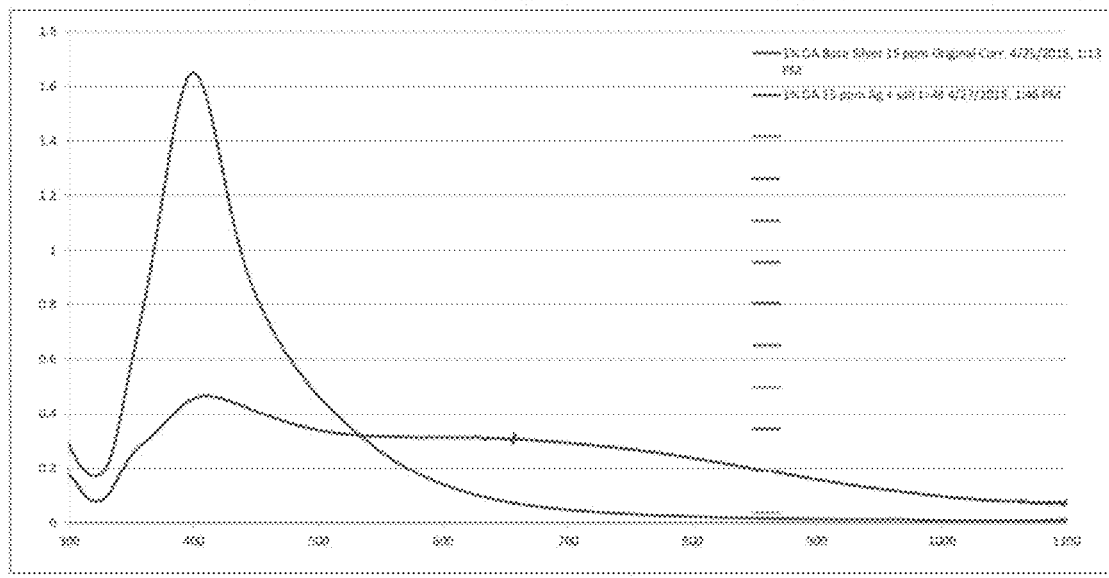
Figure 7:
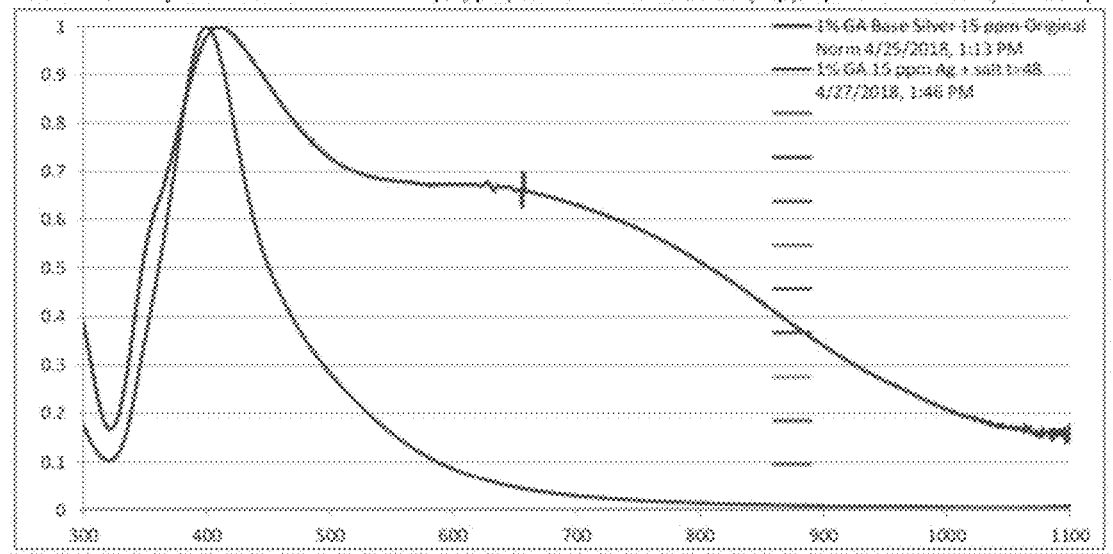

The results are plotted in FIGS. 6 and 7, for 1.0 weight % GA nanosilver (15 ppm) and for 1.0 weight % GA nanosilver (15 ppm) with the addition of 1.0 weight % calcium chloride (CaCl$_2$)). As shown in FIGS. 6 and 7, the results without CaCl$_2$) have a peak of satisfactory results while the plot for the process in the presence of the CaCl$_2$) still shows rather poor, unsatisfactory results in the form of a normalized and dilution corrected charts (FIGS. 6 and 7).

Synthesis of Gum Arabic Encapsulated Silver
Nanoparticles—2.5% GA 2.5 weight % of gum arabic (GA) (1.25 g/50 mL Solution) is dissolved in de-ionized (DI) water (or distilled water) at room temperature with continuous stirring with a magnetic stirring bar. Silver salt is then added to the GA solution as 0.5 weight % (0.25 g AgNO$_3$/50 mL solution) of the solution, followed by a sodium hydroxide solution 1.0 weight % of NaOH (0.5 g/50 mL of solution, often added to ~5 mL-10 mL of deionized water first) while being continuously stirred with a magnetic stirring bar.

After 24 hours of stirring, without heating, the product formed, GAAgNPs, are analyzed by optical absorbance measurements.

Figure 8:
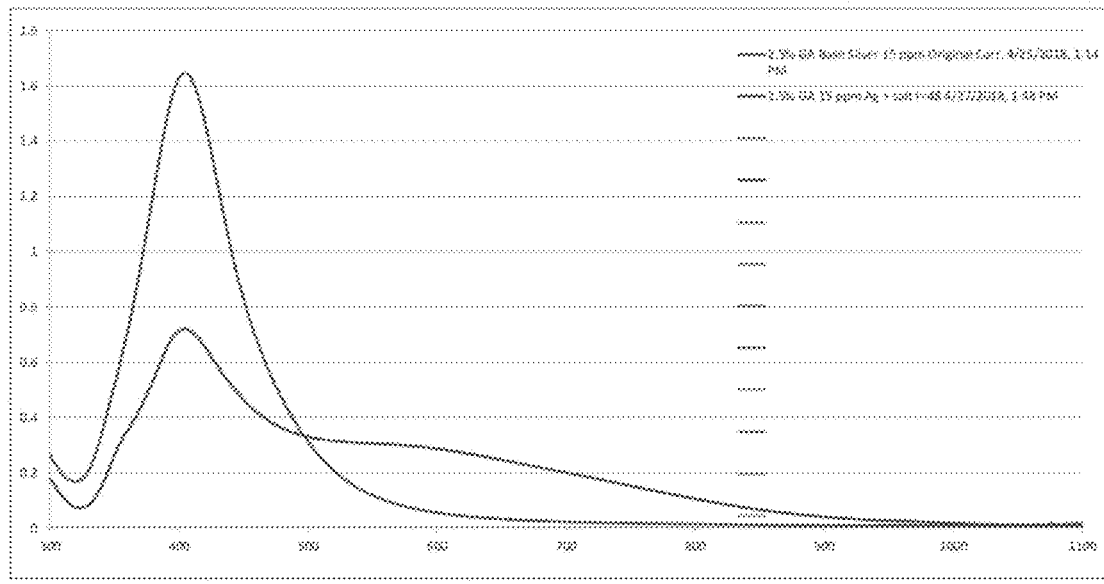
Figure 9:
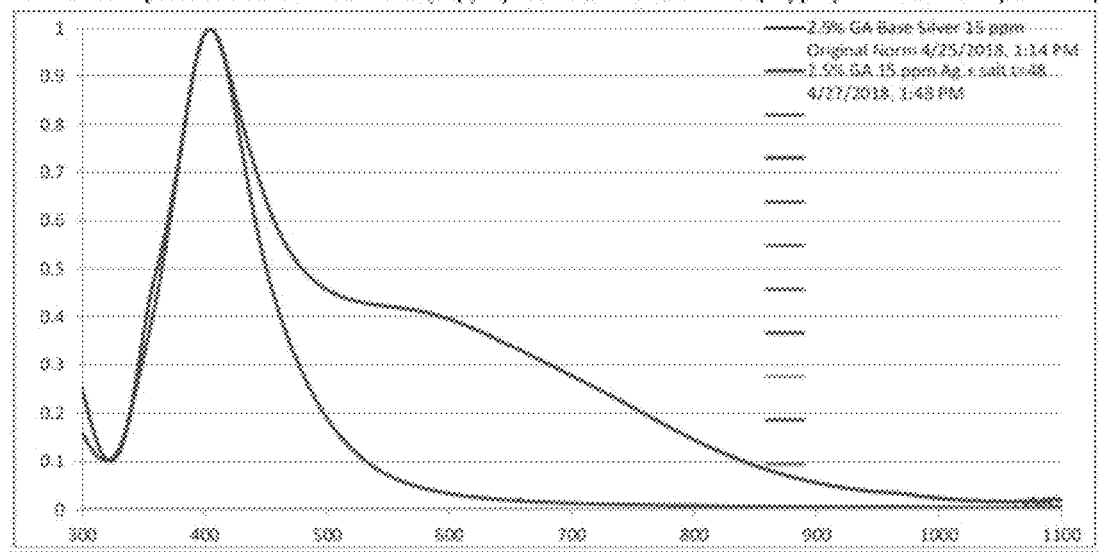

The results are plotted in FIGS. 8 and 9, for 2.5 weight % GA nanosilver (15 ppm) and for 2.5 weight % GA nanosilver (15 ppm) with the addition of 1.0 weight % calcium chloride (CaCl$_2$)). As shown in FIGS. 8 and 9, the results without CaCl$_2$) have a peak of satisfactory results while the plot for the process in the presence of the CaCl$_2$) shows rather poor, unsatisfactory results in the form of a normalized and dilution corrected charts (FIGS. 8 and 9).

Synthesis of Gum Arabic Encapsulated Silver
Nanoparticles—5.0% GA 5.0 weight % of gum arabic (GA) (2.5 g/50 mL Solution) is dissolved in de-ionized (DI) water (or distilled water) at room temperature with continuous stirring with a magnetic stirring bar. Silver salt is then added to the GA solution as 0.5 weight % (0.25 g AgNO$_3$/50 mL solution) of solution, followed by a sodium hydroxide solution 1.0 weight % of NaOH (0.5 g/50 mL of solution, often added to ~5-10 mL of deionized water first) while being continuously stirred with a magnetic stirring bar.

After 24 hours of stirring, without heating, the product formed, GAAgNPs, are analyzed by optical absorbance measurements.

Figure 10:
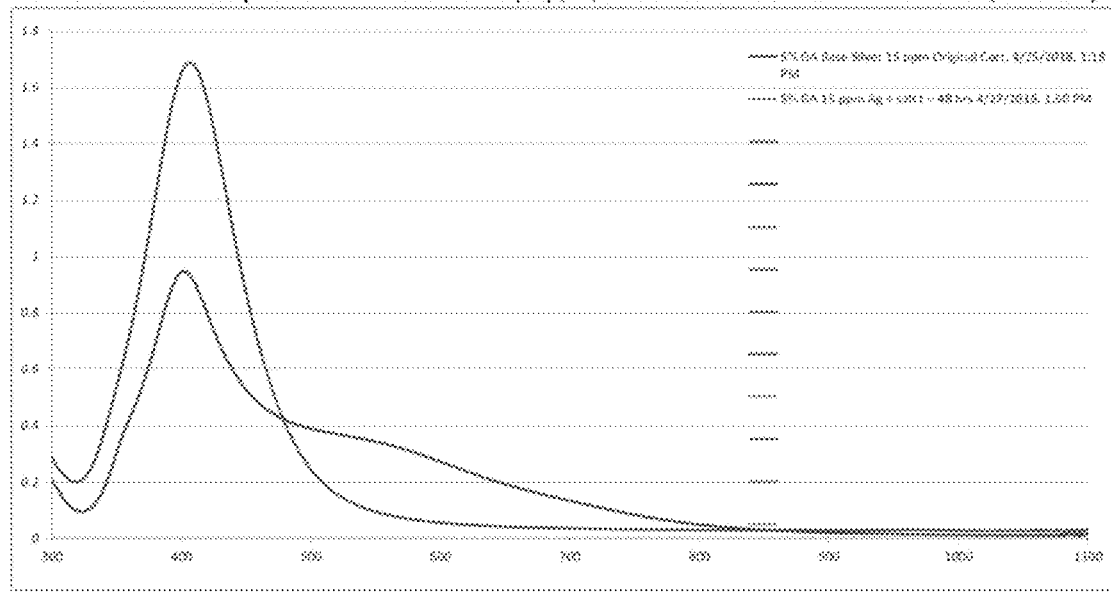
Figure 11:
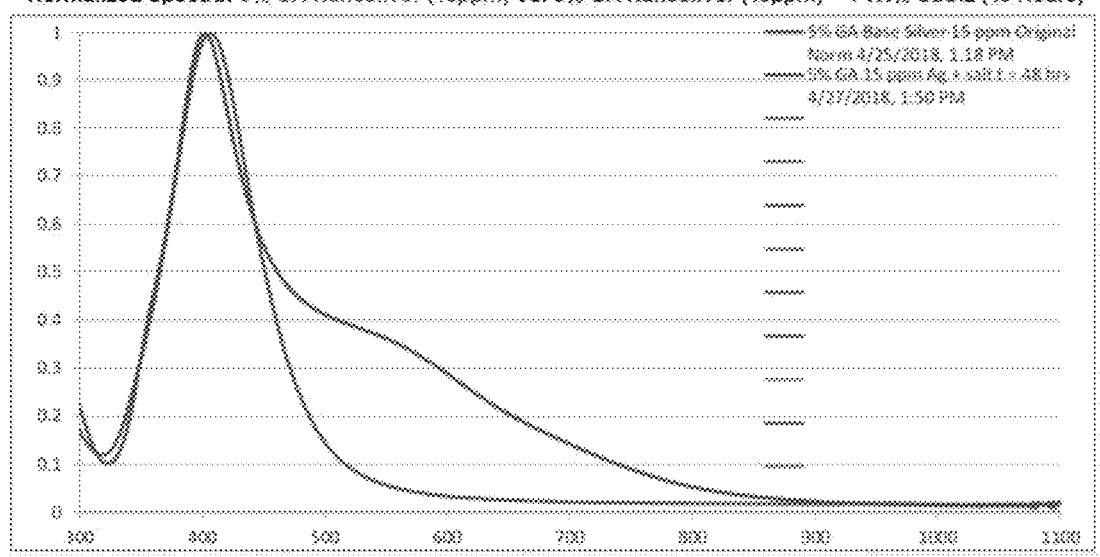

The results are plotted in FIGS. 10 and 11, for 5.0 weight % GA nanosilver (15 ppm) and for 5.0 weight % GA nanosilver (15 ppm) with the addition of 1.0 weight % calcium chloride (CaCl$_2$)). As shown in FIGS. 10 and 11, the results without CaCl$_2$) have a peak of satisfactory results while the plot for the process in the presence of the CaCl$_2$) shows rather poor, unsatisfactory results in the form of a normalized and dilution corrected charts (FIGS. 10 and 11).

Synthesis of Gum Arabic Encapsulated Silver
Nanoparticles—7.5% GA 7.5 weight % of gum arabic (GA) (3.75 g/50 mL Solution) is dissolved in de-ionized (DI) water (or distilled water) at room temperature with continuous stirring with a magnetic stirring bar. Silver salt is then added to the GA solution as 0.5 weight % (0.25 g AgNO$_3$/50 mL solution), followed by a sodium hydroxide solution 1.0 weight % of NaOH (0.5 g/50 mL of solution, often added to ~5-10 mL of deionized water first) while being continuously stirred with a magnetic stirring bar.

After 24 hours of stirring, without heating, the product formed, GAAgNPs, are analyzed by optical absorbance measurements.

Figure 12:
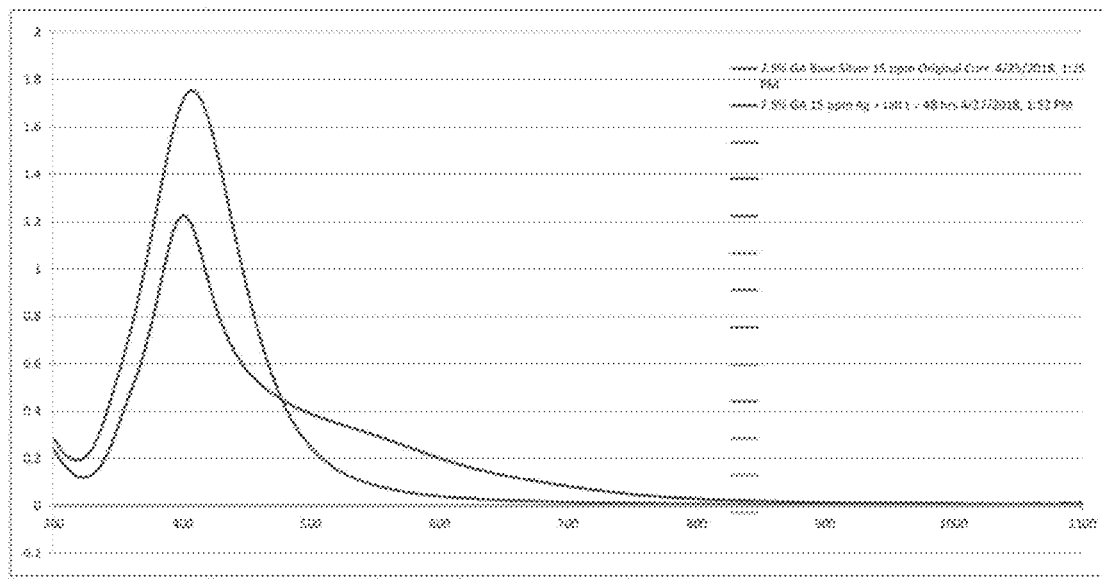
Figure 13:
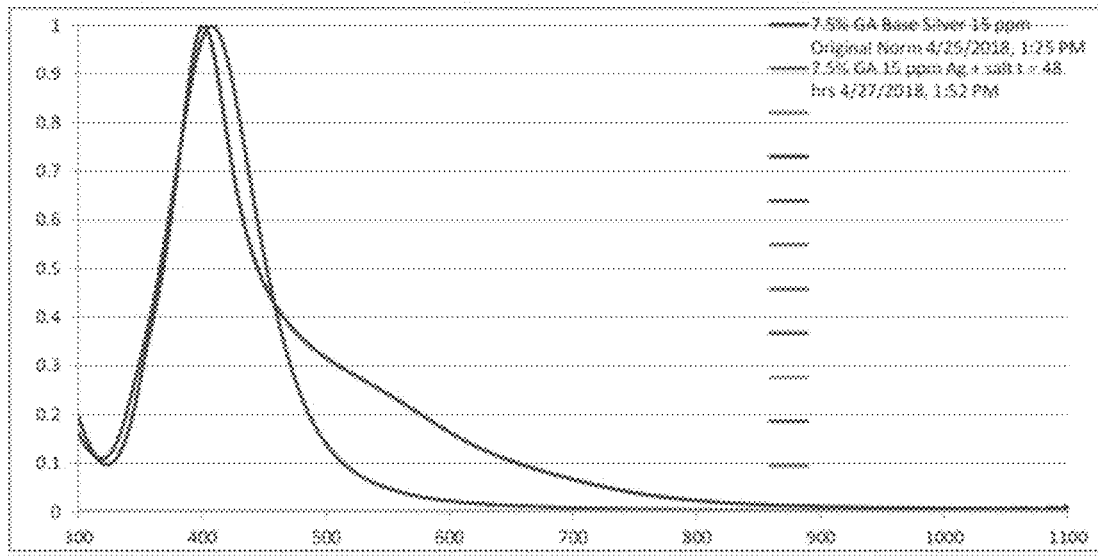

The results are plotted in FIGS. 12 and 13, for 7.5 weight % GA nanosilver (15 ppm) and for 7.5 weight % GA nanosilver (15 ppm) with the addition of 1.0 weight % calcium chloride (CaCl$_2$)). As shown in FIGS. 12 and 13, the results without CaCl$_2$) have a peak of satisfactory results while the plot for the process in the presence of the CaCl$_2$) shows marginally better results than in the experiments using lower concentrations of GA in the form of a normalized and dilution corrected charts (FIGS. 12 and 13).

Synthesis of Gum Arabic Encapsulated Silver
Nanoparticles 10% GA 10.0 weight % of gum arabic (GA) (5.0 g/50 mL Solution) is dissolved in de-ionized (DI) water (or distilled water) at room temperature with continuous stirring with a magnetic stirring bar. Silver salt is then added to the GA solution as 0.5 weight % (0.25 g AgNO$_3$/50 mL solution) of solution, followed by a sodium hydroxide solution 1.0 weight % of NaOH (0.5 g/50 mL of solution, often added to ~5-10 mL of deionized water first) while being continuously stirred with a magnetic stirring bar.

After 24 hours of stirring, without heating, the product formed, GAAgNPs, are analyzed by optical absorbance measurements.

Figure 14:
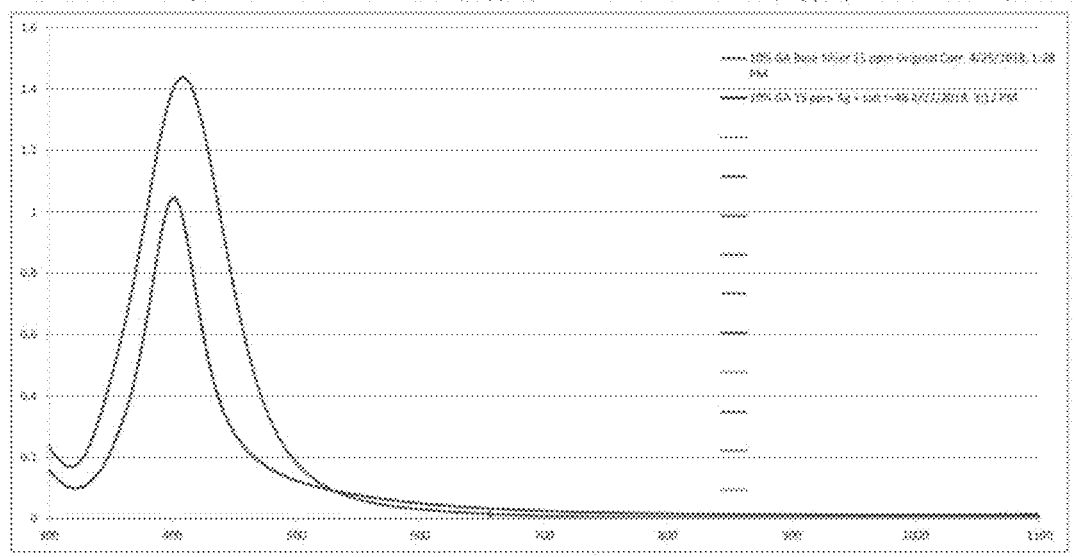
Figure 15:
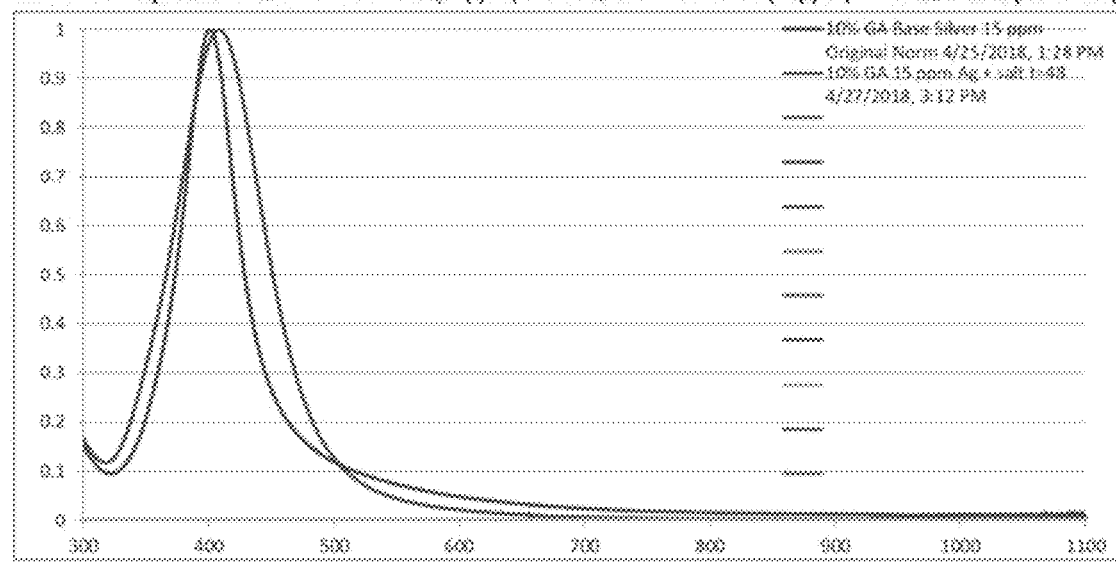

The results are plotted in FIGS. 14 and 15, for 10.0 weight % GA nanosilver (15 ppm) and for 10.0 weight % GA nanosilver (15 ppm) with the addition of 1.0 weight % calcium chloride ($CaCl_2$)). As shown in FIGS. 14 and 15, the results without $CaCl_2$) have a peak of satisfactory results while the plot for the process in the presence of the $CaCl_2$ shows results more satisfactory than prior, lower gum concentration experiments in the form of a normalized and dilution corrected charts (FIGS. 14 and 15).

Synthesis of Gum Arabic Encapsulated Silver Nanoparticles 12.5% GA 12.5 weight % of gum arabic (GA) (6.25 g/50 mL Solution) is dissolved in de-ionized (DI) water (or distilled water) at room temperature with continuous stirring with a magnetic stirring bar. Silver salt is then added to the GA solution as 0.5 weight % (0.25 g $AgNO_3$/50 mL solution) of solution, followed by a sodium hydroxide solution 1.0 weight % of NaOH (0.5 g/50 mL of solution, often added to ~5-10 mL of deionized water first) while being continuously stirred with a magnetic stirring bar.

After 24 hours of stirring, without heating, the product formed, GAAgNPs, are analyzed by optical absorbance measurements.

Figure 16:
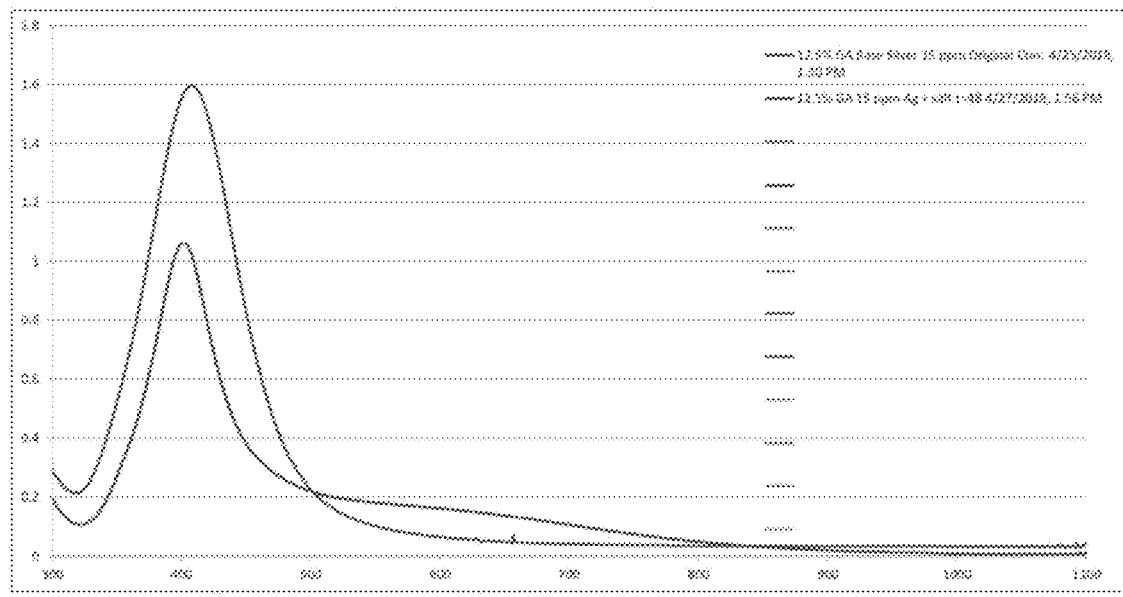
Figure 17:
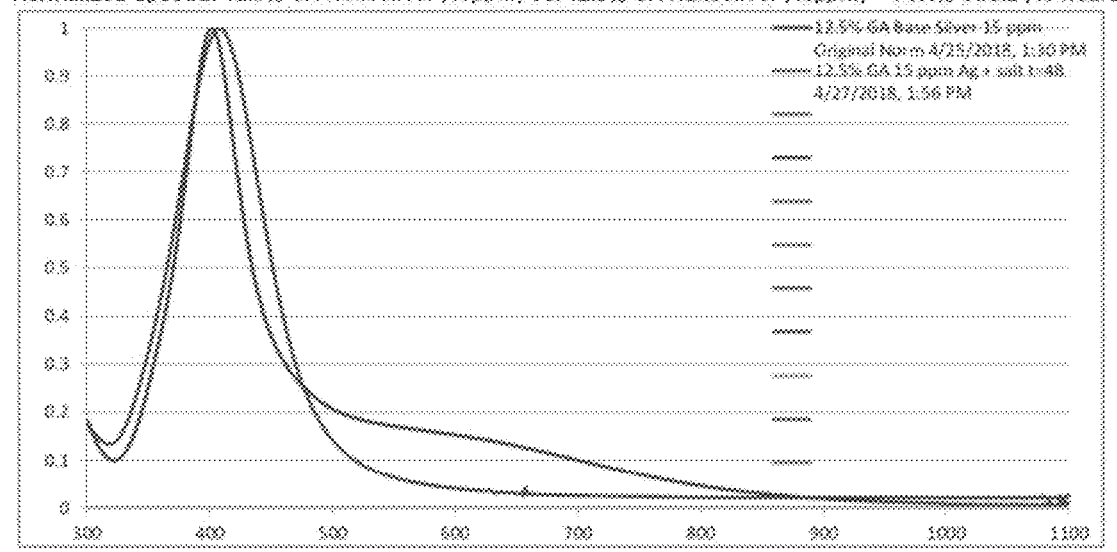

The results are plotted in FIGS. 16 and 17, for 12.5 weight % GA nanosilver (15 ppm) and for 12.5 weight % GA nanosilver (15 ppm) with the addition of 1.0 weight % calcium chloride ($CaCl_2$)). As shown in FIGS. 16 and 17, the results without $CaCl_2$) have a peak of satisfactory results while the plot for the process in the presence of the $CaCl_2$) shows results indicating that this method avoids poor results even in the presence of calcium chloride in the form of normalized charts and dilution corrected charts (FIGS. 16 and 17).

Synthesis of Gum Arabic Encapsulated Silver Nanoparticles 15% GA 15.0 weight % of gum arabic (GA) (7.5 g/50 mL solution) is dissolved in de-ionized (DI) water (or distilled water) at room temperature with continuous stirring with a magnetic stirring bar. Silver salt is then added to the GA solution as 0.5 weight % (0.25 g $AgNO_3$/50 mL solution), followed by aسodium hydroxide solution (1.0 weight %) of NaOH (0.5 g/50 mL of solution, often added to ~5-10 mL of deionized water first) while being continuously stirred with a magnetic stirring bar.

After 24 hours of stirring, without heating, the product formed, GAAgNPs, are analyzed by optical absorbance measurements.

Figure 18:
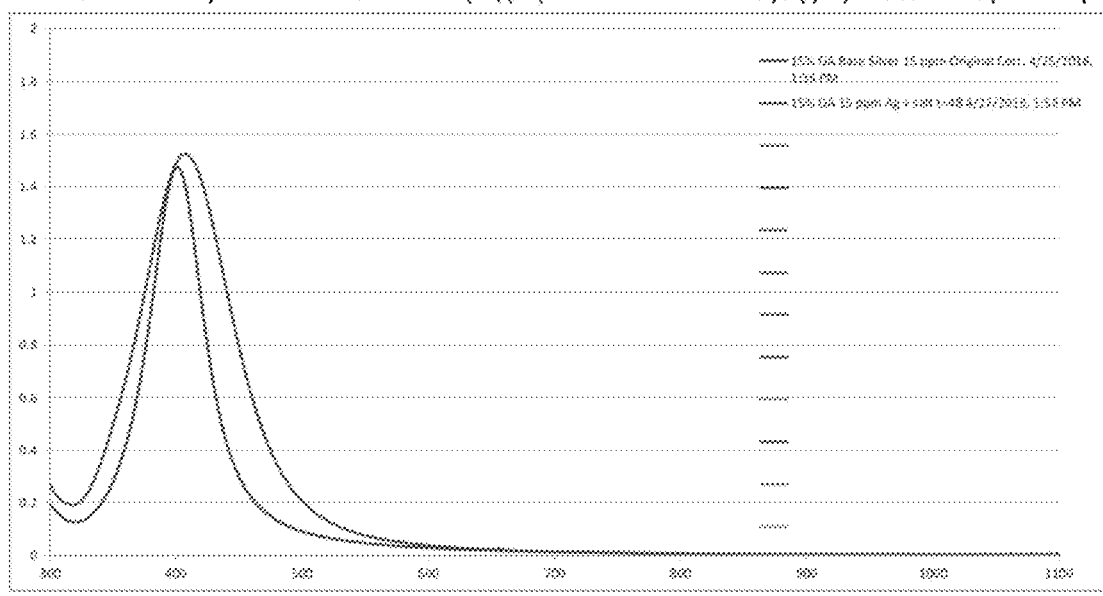
Figure 19:
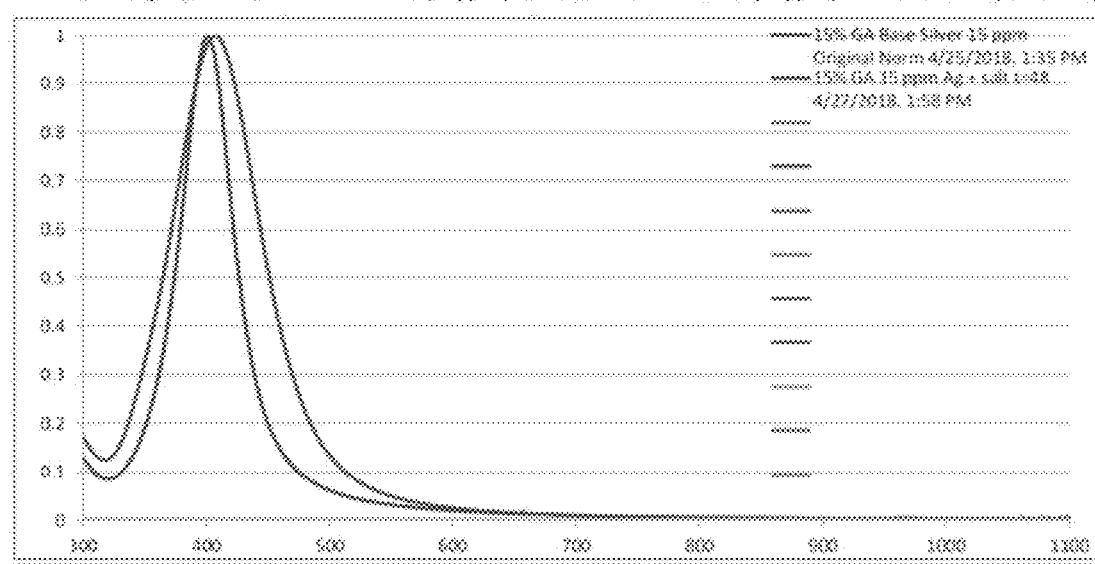

The results are plotted in FIGS. 18 and 19, for 15 weight % GA nanosilver (15 ppm) and for 15 weight % GA nanosilver (15 ppm) with the addition of 1.0 weight % calcium chloride ($CaCl_2$)). As shown in FIGS. 18 and 19, the results without $CaCl_2$) have a peak of satisfactory results while the plot for the process in the presence of the $CaCl_2$) shows satisfactory results even in the presence of $CaCl_2$) in the form of a normalized and dilution corrected charts (FIGS. 18 and 19).

Gum Arabic Encapsulated Silver Nanoparticles 15% GA Stability-Stainless Steel 15.0 weight % of gum arabic (GA) (7.5 g/50 mL Solution) is dissolved in de-ionized (DI) water (or distilled water) at room temperature with continuous stirring with a magnetic stirring bar. Silver salt is then added to the GA solution as 0.5 weight % (0.25 g $AgNO_3$/50 mL solution) of solution, followed by a sodium hydroxide solution (1.0 weight %) of NaOH (0.5 g/50 mL of solution, often added to ~5-10 mL of deionized water first) while being continuously stirred with a magnetic stirring bar.

After 24 hours of stirring, without heating, the product formed, GAAgNPs, are analyzed by optical absorbance measurements.

Figure 20:
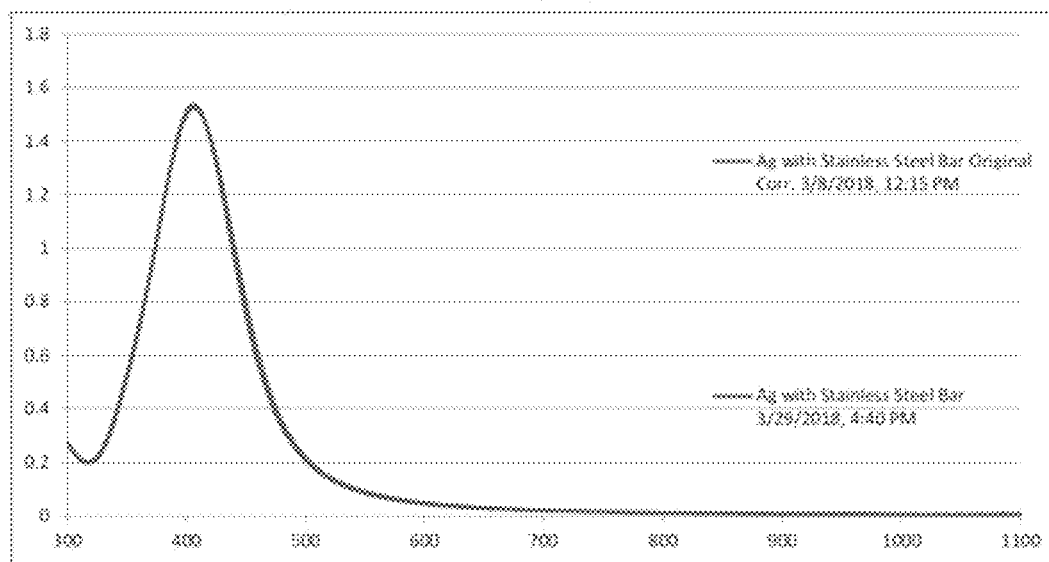
Figure 21:
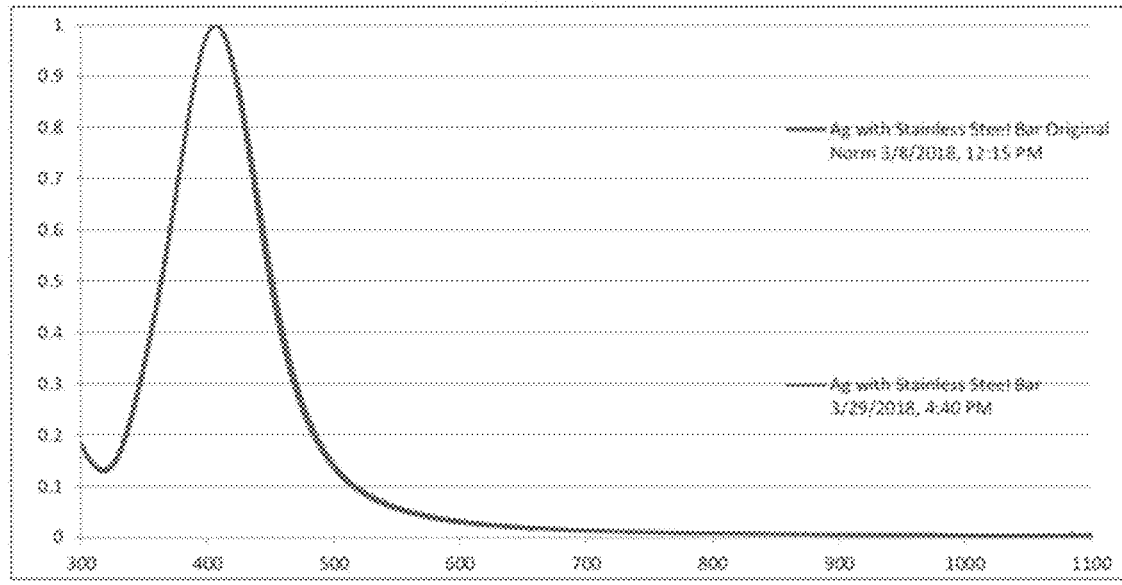

The results are plotted, for 15 weight % GA nanosilver (20 ppm) and for 15 weight % GA nanosilver (20 ppm) with a bar of stainless steel (grade 316). As shown in the plots in FIGS. 20 and 21, the results are satisfactory, showing insignificant changes even after three weeks. This is shown in the form of normalized and dilution corrected charts (Plots 20,21) showing satisfactory experimental results for gum arabic synthesized silver nanoparticles stability in the presence of stainless steel, a common component in storage, packaging and filling machinery, another embodiment of the present invention:

Gum Arabic Encapsulated Silver Nanoparticles 15% GA Stability-Xylitol/Calcium Salt Experiment 15.0 weight % of gum arabic (GA) (7.5 g/50 mL Solution)] is dissolved in de-ionized (DI) water (or distilled water) at room temperature with continuous stirring with a magnetic stirring bar. Silver salt is then added to the GA solution as 0.5 weight % (0.25 g $AgNO_3$/50 mL solution) of solution, followed by a sodium hydroxide solution 1.0 weight % of NaOH (0.5 g/50 mL of solution, often added to ~5-10 mL of deionized water first) while being continuously stirred with a magnetic stirring bar.

After 24 hours of stirring, without heating, the product formed, GAAgNPs, are analyzed by optical absorbance measurements.

Figure 22:
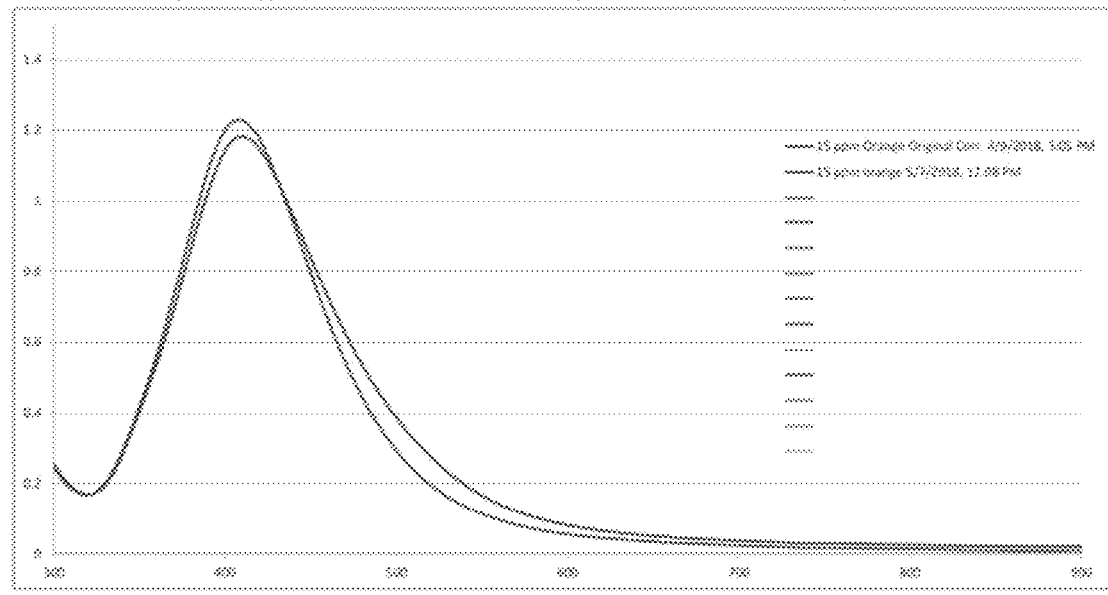
Figure 23:
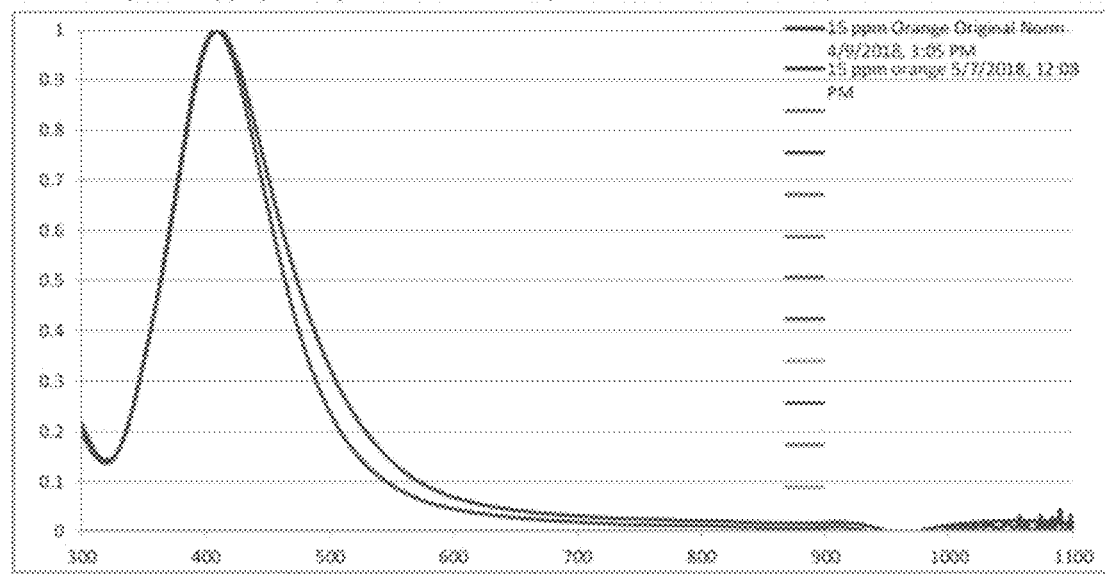

The results are plotted in FIGS. 22 and 23, for 15.0 weight % GA nanosilver (15 ppm) and for 15 weight % GA nanosilver (15 ppm) with 25% xylitol and 0.9% calcium acetate showing minimal changes even after 4 weeks. This is shown in the form of a normalized and dilution corrected charts. FIGS. 22 and 23 show satisfactory experimental results for gum arabic synthesized silver nanoparticles stability in the presence of an osmolyte (xylitol) at high percentage, in addition to calcium salt another embodiment of the present invention.

Gum Arabic Encapsulated Silver Nanoparticles 15% GA Stability-Sodium Fluoride 15.0 weight % of gum arabic (GA) (7.5 g/50 mL solution) is dissolved in de-ionized (DI) water (or distilled water) at room temperature with continuous stirring with a magnetic stirring bar. Silver salt is then added to the GA solution as 0.5 weight % (0.25 g $AgNO_3$/50 mL solution) of solution, followed by a sodium hydroxide solution 1.0 weight % of NaOH (0.5 g/50 mL of solution, often added to ~5-10 mL of deionized water first) while being continuously stirred with a magnetic stirring bar.

After 24 hours of stirring, without heating, the product formed, GAAgNPs, are analyzed by optical absorbance measurements.

Figure 24:
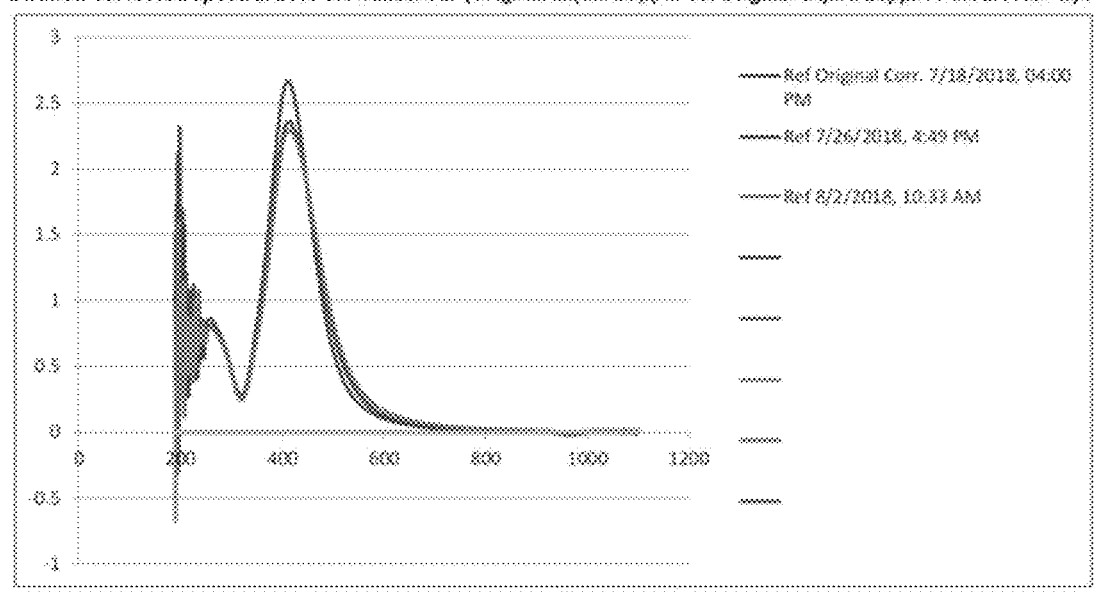
Figure 25:
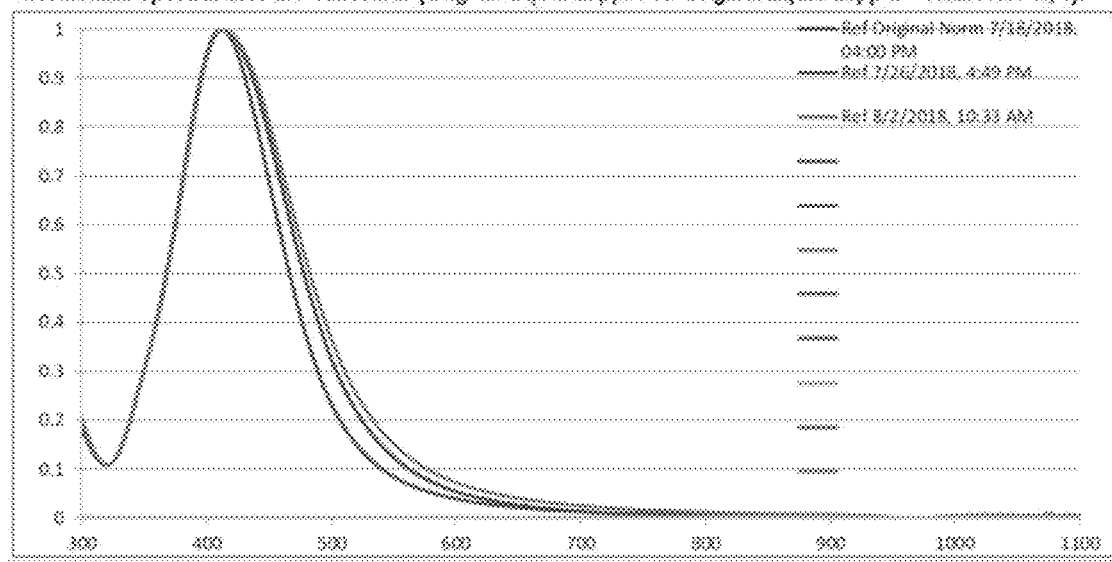
Figure 26:
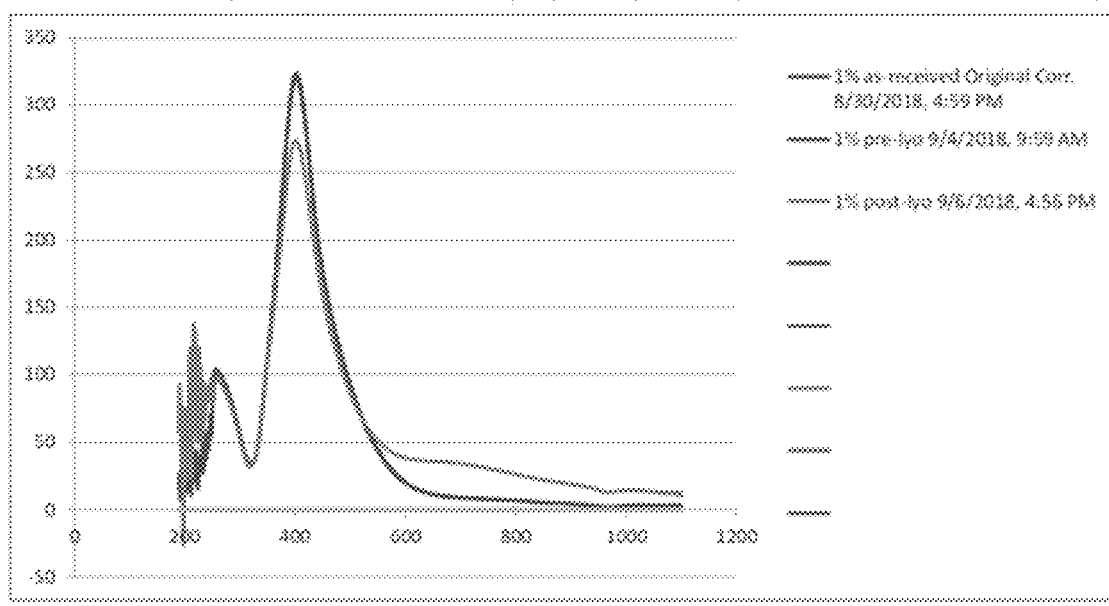
Figure 27:
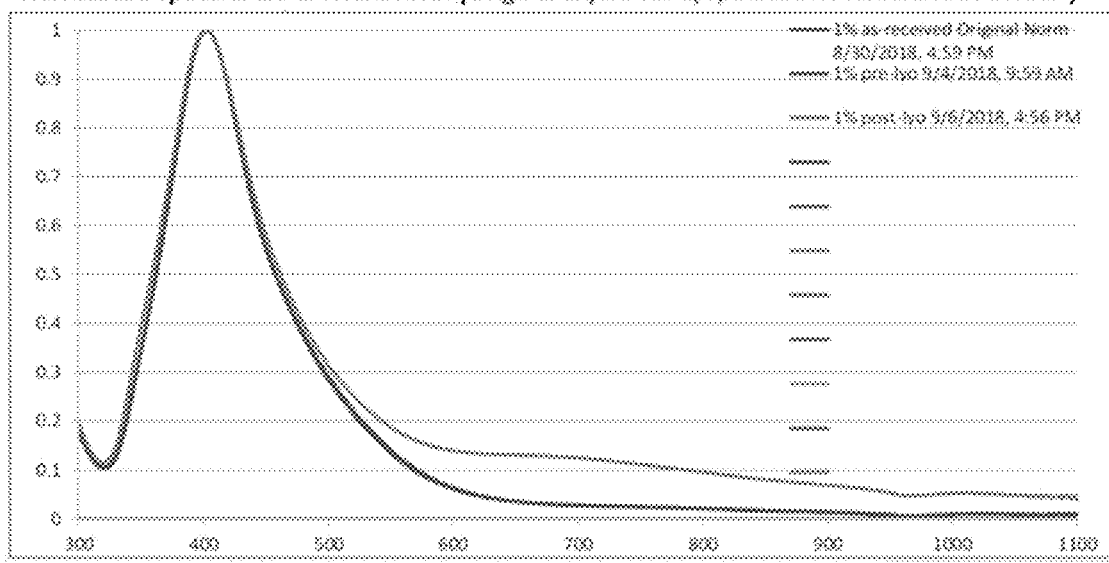
Figure 28:
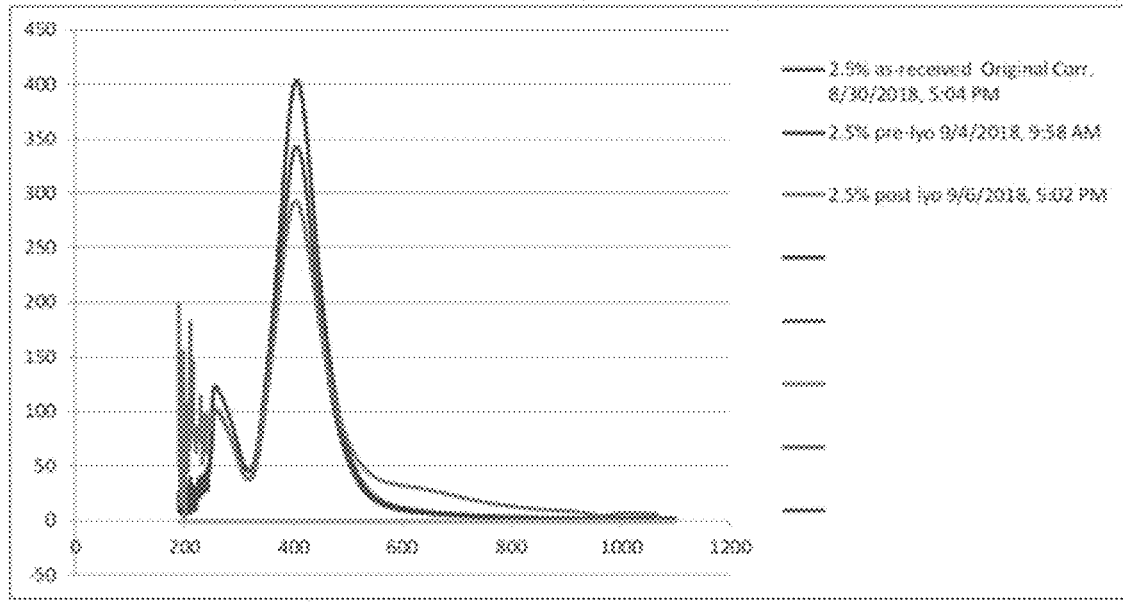
Figure 29:
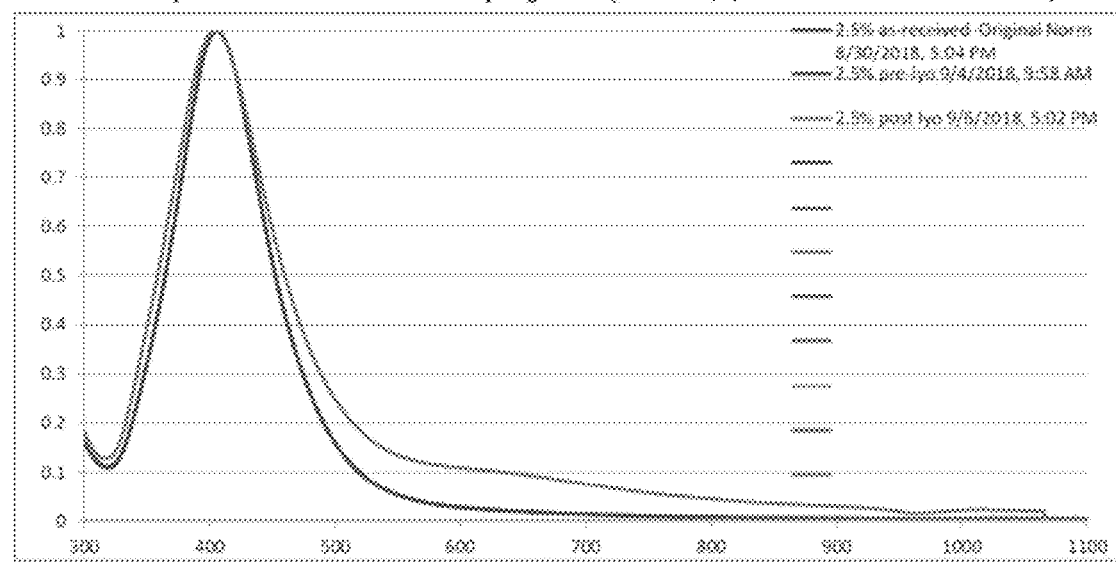
Figure 30:
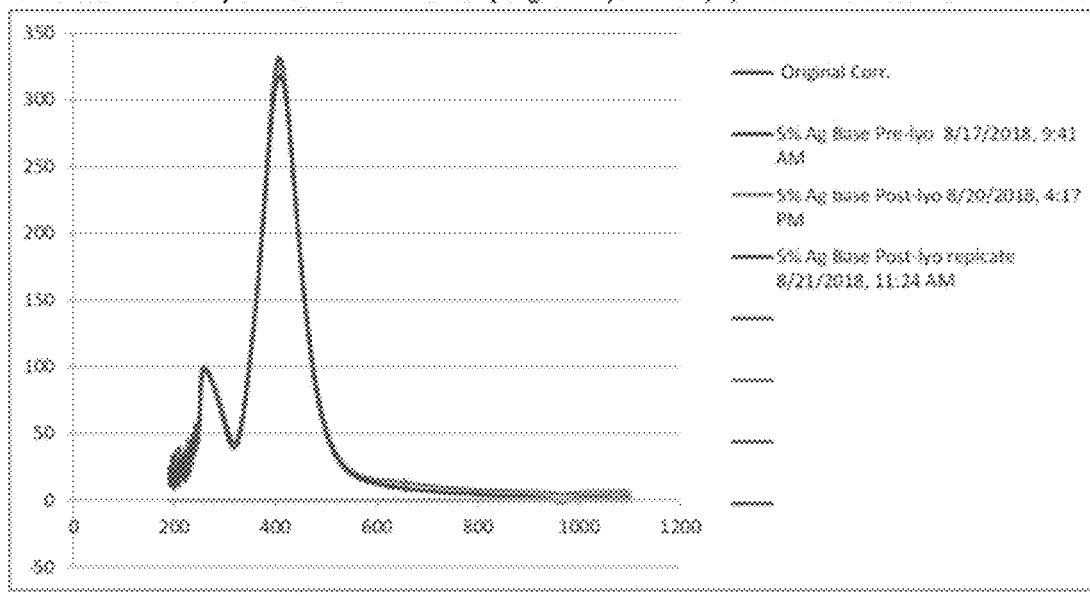
Figure 31:
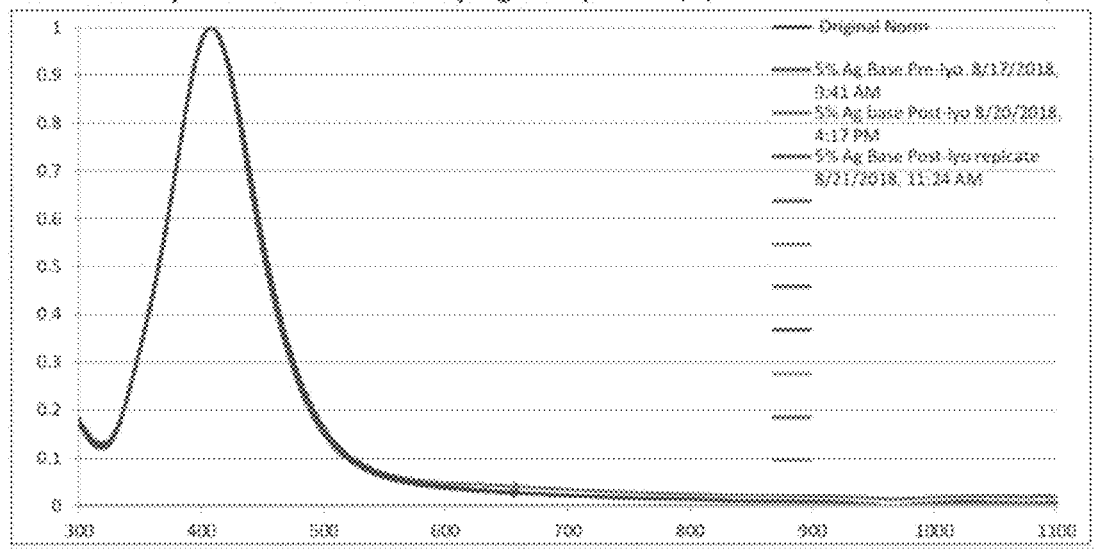
Figure 32:
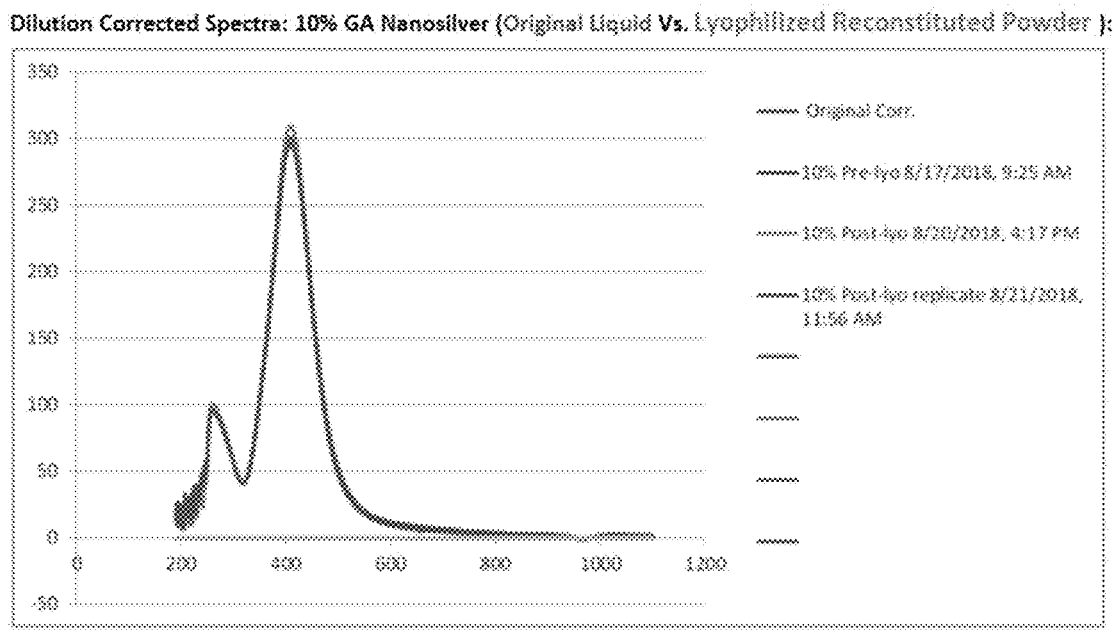
Figure 33:
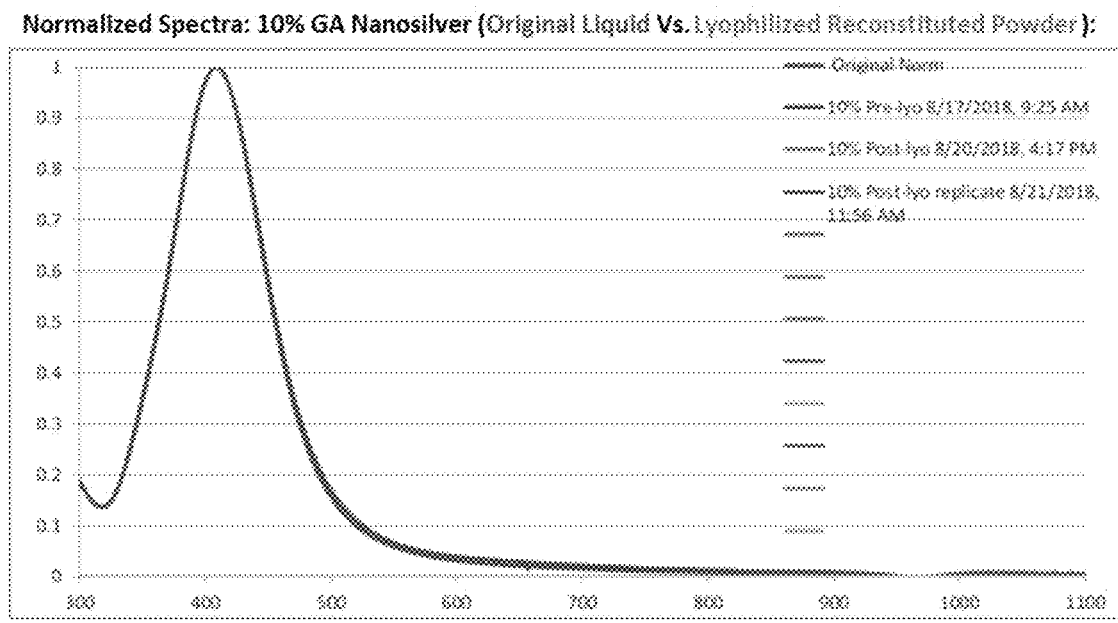
Figure 34:
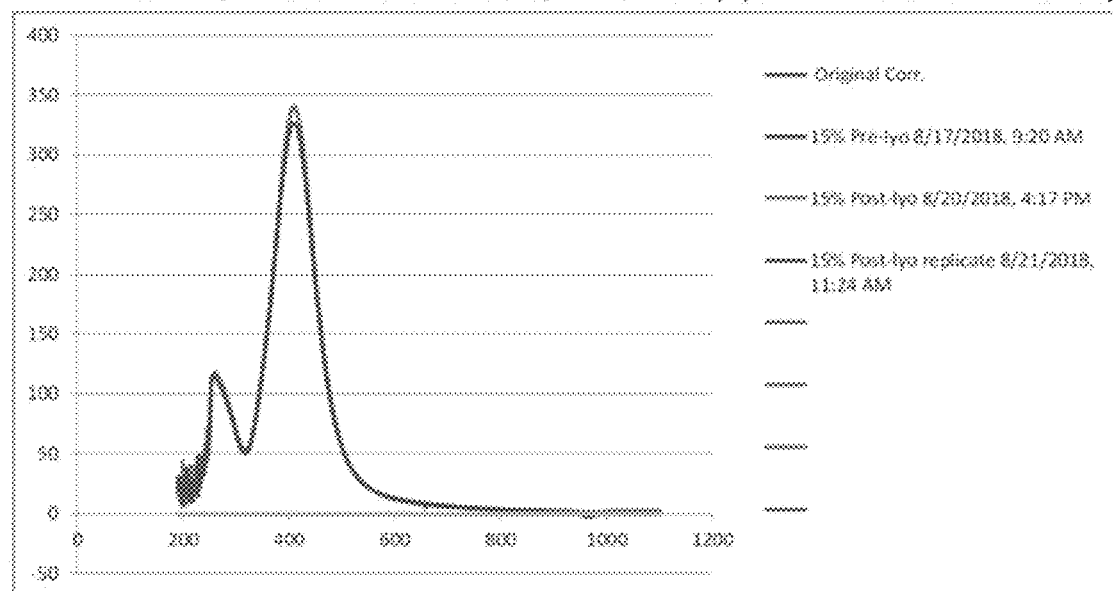
Figure 35:
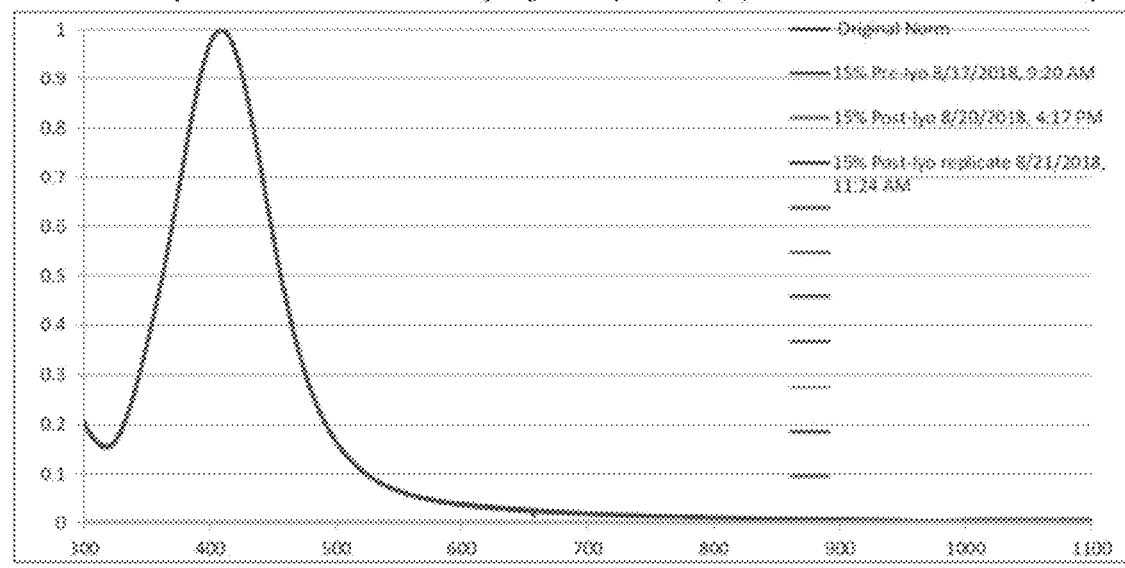

The results are plotted in FIGS. 24 and 25, for 15 weight % GA nanosilver (20 ppm) and for 15 weight % GA nanosilver (20 ppm) with 0.02% NaF. As shown in the plots, after 1 and 2 weeks the results are satisfactory, showing minimal changes. This is shown in the form of a normalized and dilution corrected charts (Plots 24, 25) showing experimental results for gum arabic synthesized silver nanoparticles stability in the presence of a salt used for dental preventative agents, another embodiment of the present invention:

Gum Arabic Encapsulated Silver Nanoparticles Synthesized with GA Stability after Lyophilization A varying GA Wt %=X, where X=1.0, 2.5, 5.0, 10.0 or 15.0% of gum arabic (GA) (Where "X" g/50 mL solution=0.5 g, 1.25 g, 2.5 g, 5.0 g, 7.5 g GA respectively) is dissolved in de-ionized (DI) water (or distilled water) at room temperature with continuous stirring with a magnetic stirring bar. Silver salt is then added to the GA solution as 0.5 weight % (0.25 g AgNO$_3$/50 mL solution), followed by a sodium hydroxide solution 1.0 weight % of NaOH (0.5 g/50 mL of solution, often added to ~5-10 mL of deionized water first) while being continuously stirred with a magnetic stirring bar.

After 24 hours of stirring, without heating, the product formed, GAAgNPs, are analyzed by optical absorbance measurements.

The results are plotted in FIGS. 26-35, for 1.0, 2.5, 5.0, 10.0 and 15.0 weight % GA synthesized nanosilver. The results are satisfactory after 5.0 weight % GA, showing minimal changes even after lyophilization. Below 5.0 weight % results are unsatisfactory, showing deviations from the original baseline synthesized nanosilver product. This is shown in the form of a normalized and dilution corrected charts in which the powder is reconstituted into water and re-examined compared to the original sample. (FIGS. 26-35):

Exemplary proportions for baseline preparation are provided in Table 3.

TABLE 3

NANOSILVER BASELINE REFERENCE
Lyophilization preparation:

| Sample: (GAAgNP samples derived from synthesis from table 1) | Nanosilver: BASELINE REFERENCE: |
|---|---|
| GA-BASE(1) | 1% GA Sample |
| GA-BASE(2.5) | 2.5% GA Sample |
| GA-BASE(5) | 5% GA Sample |
| GA-BASE(10) | 10% GA Sample |
| GA-BASE(15) | 15% GA Sample |

FIGS. 36-65 & tables 4-9 contain synthesis information and show experimental results for various gum arabic concentrations when preparing gold nanoparticles encapsulated in gum arabic plots show absorbance (Y-axis) vs. wavelength (X-axis).

Synthesis of Gum Arabic Encapsulated Gold Nanoparticles—0.5% GA 0.5 weight % of gum arabic (GA) (0.25 g/50 mL solution) is dissolved in de-ionized (DI) water (or distilled water) at room temperature with continuous stirring with a magnetic stirring bar. Gold salt (HAuCl$_4$) is then added to the GA solution as 0.5 weight % (0.0147 M HAuCl$_4$), followed by a sodium hydroxide solution 1 weight % of NaOH (0.5 g/50 mL solution, often added to ~5-10 mL of deionized water first) while being continuously stirred with a magnetic stirring bar.

After 24 hours of stirring, without heating, the product formed, GAAuNPs, are analyzed by optical absorbance measurements.

Figure 36:
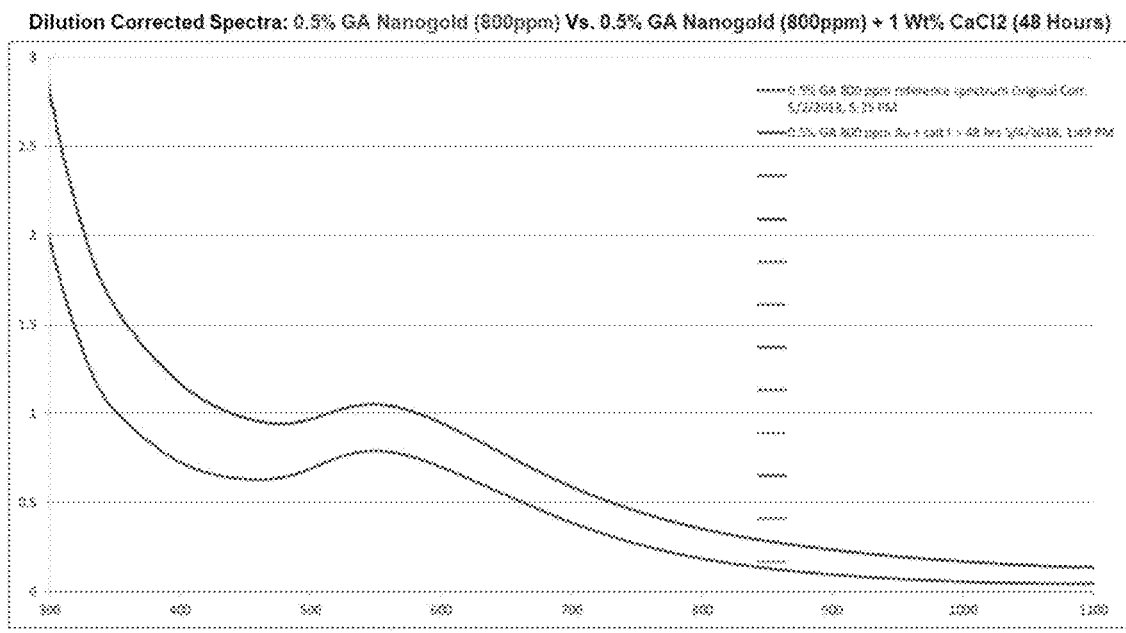
Figure 37:
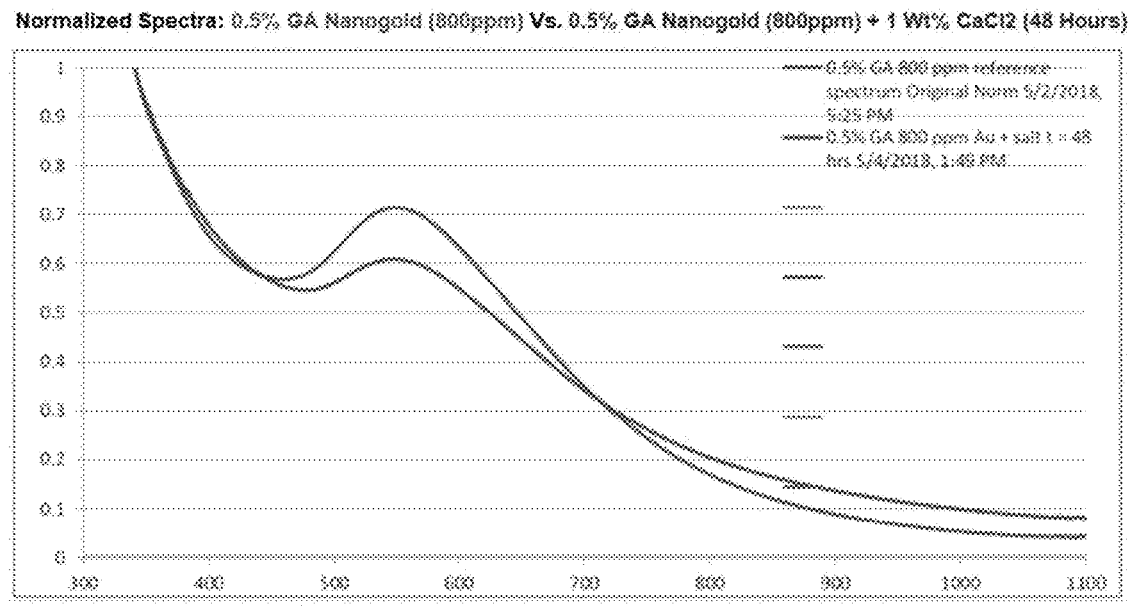

The results are plotted in FIGS. 36 and 37, for 0.5 weight % GA nanogold (800 ppm) and for 0.5 weight % GA nanogold (800 ppm) with the addition of 1.0 weight % calcium chloride (CaCl$_2$)). As shown in FIGS. 36 and 37, the results without CaCl$_2$) have a peak of unsatisfactory results while the plot for the process in the presence of the CaCl$_2$) also shows rather poor, unsatisfactory results in the form of a normalized and dilution corrected charts (FIGS. 36, 37).

Representative proportions are provided in Table 4.

TABLE 4

Synthesis of GA Gold Nanoparticles(GAAuNPs) with varying Wt % GA:

| Sample: | Gold Salt (HAuCl$_4$ Wt %) | Gum Arabic (Wt %) | Ratio of Gum:Salt | Accelerator (NaOH) |
|---|---|---|---|---|
| GldGA-BASE (.5) | .5% (0.25 g or 0.0147M) HAuCl$_4$ solution/50 mL | .5% (0.25 g/50 mL) | 1:1 | 1% (0.5 g/50 mL) |
| GldGA-BASE (1) | .5% | 1% (0.5 g/50 mL) | 2:1 | 1% |
| GldGA-BASE (2.5) | .5% | 2.5% (1.25 g/50 mL) | 5:1 | 1% |
| GldGA-BASE (5) | .5% | 5% (2.5 g/50 mL) | 10:1 | 1% |
| GldGA-BASE (10) | .5% | 10% (5 g/50 mL) | 20:1 | 1% |
| GldGA-BASE (15) | .5% | 15% (7.5 g/50 mL) | 30:1 | 1% |

Representative proportions for nanogold with salt concentrations are provided in Table 5.

TABLE 5

GA NANOGOLD Salt study EXPERIMENTAL SAMPLES with 1 Wt % $CaCl_2$:

| Sample: (GAAuNP Samples Derived from Synthesis in Table 4) | Nanogold + H2O + 1 Wt % $CaCl_2$ EXPERIMENTAL SALT TRIAL |
| --- | --- |
| GldGA-CAL(.5) | .5% GA Sample (800 ppm) |
| GldGA-CAL(1) | 1% GA Sample (400 ppm) |
| GldGA-CAL(2.5) | 2.5% GA Sample (200 ppm) |
| GldGA-CAL(5) | 5% GA Sample (200 ppm) |
| GldGA-CAL-(10) | 10% GA Sample (200 ppm) |
| Gld GA-CAL-(15) | 15% GA Sample (200 ppm) |

Representative proportions from a baseline are provided in Table 6.

TABLE 6

NANOGOLD BASELINE REFERENCE:

| Sample: (GAAuNP Samples Derived from Synthesis in Table 4) | Nanogold + H2O: BASELINE REFERENCE |
| --- | --- |
| GldGA(.5) | .5% GA Sample (800 ppm) |
| GldGA(1) | 1% GA Sample (400 ppm) |
| GldGA(2.5) | 2.5% GA Sample (200 ppm) |
| GldGA(5) | 5% GA Sample (200 ppm) |
| GldGA(10) | 10% GA Sample (200 ppm) |
| GldGA(15) | 15% GA Sample (200 ppm) |

Synthesis of Gum Arabic Encapsulated Gold Nanoparticles—1.0% GA 1.0 weight % of gum arabic (GA) (0.5 g/50 mL solution) is dissolved in de-ionized (DI) water (or distilled water) at room temperature with continuous stirring with a magnetic stirring bar. Gold salt ($HAuCl_4$) is then added to the GA solution as 0.5 weight % (0.0147 M $HAuCl_4$), followed by a sodium hydroxide solution 1.0 weight % of NaOH (0.5 g/50 mL solution, often added to ~5-10 mL of deionized water first) while being continuously stirred with a magnetic stirring bar.

After 24 hours of stirring, without heating, the product formed, GAAuNPs, are analyzed by optical absorbance measurements.

Figure 38:
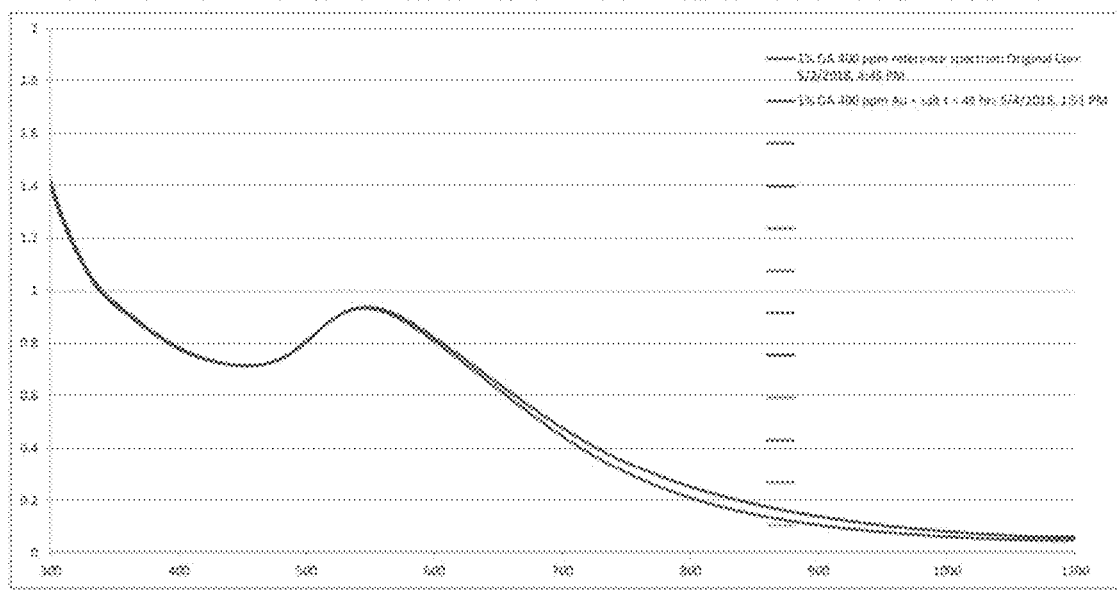
Figure 39:
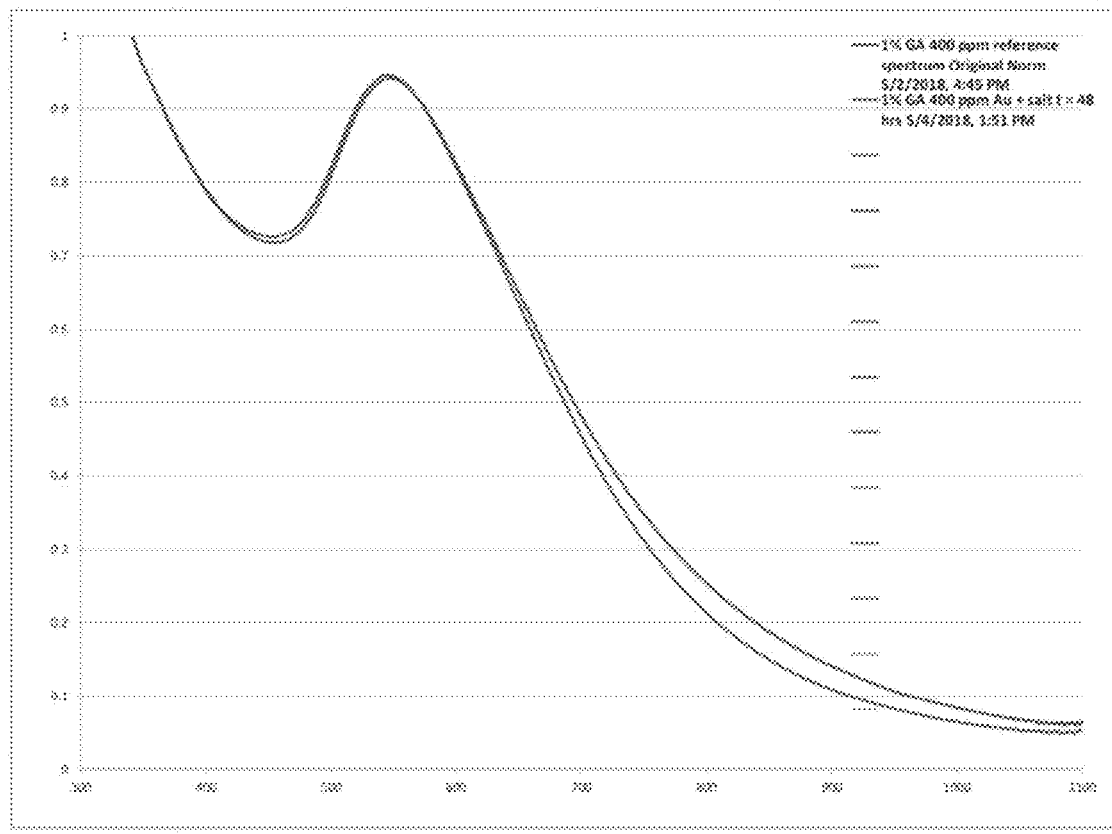

The results are plotted in FIGS. 38 and 39, for 1.0 weight % GA nanogold (400 ppm) and for 1.0 weight % GA nanogold (400 ppm) with the addition of 1.0 weight % calcium chloride ($CaCl_2$)). As shown in FIGS. 38 and 39, the results without $CaCl_2$) have a peak of somewhat satisfactory results whereas with the $CaCl_2$) likewise have marginal, somewhat satisfactory results (Although not much shifting occurred, the peaks are not well defined) in the form of a normalized and dilution corrected charts (FIGS. 38 and 39).

Synthesis of Gum Arabic Encapsulated Gold Nanoparticles—5.0% GA 5.0 weight % of gum arabic (GA) (2.5 g/50 mL solution) is dissolved in de-ionized (DI) water (or distilled water) at room temperature with continuous stirring with a magnetic stirring bar. Gold salt ($HAuCl_4$) is then added to the GA solution as 0.5 weight % (0.0147M $HAuCl_4$), followed by a sodium hydroxide solution 1.0 weight % of NaOH (0.5 g/50 mL solution, often added to ~5-10 mL of deionized water first) while continuously stirred with a magnetic stirring bar.

After 24 hours of stirring, without heating, the product formed, GAAuNPs, are analyzed by optical absorbance measurements.

Figure 40:
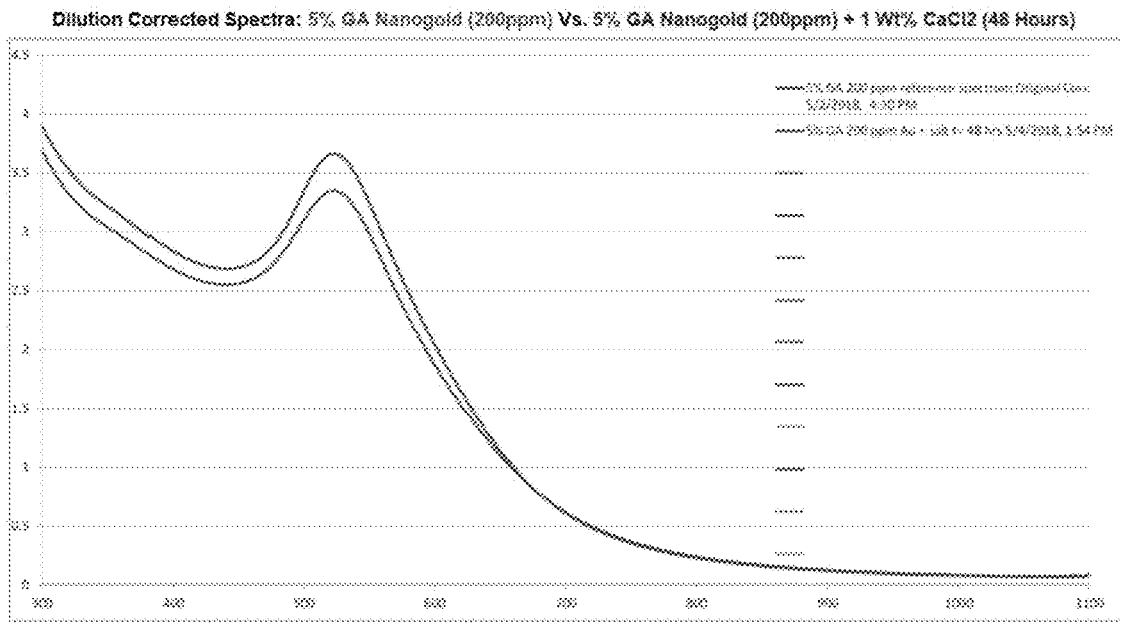
Figure 41:
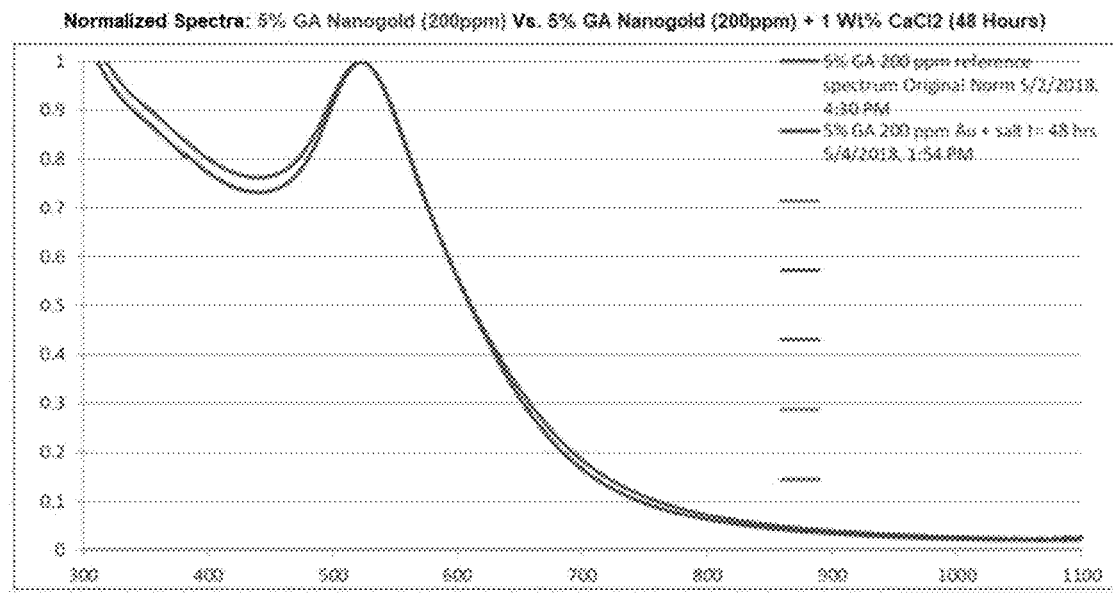

The results are plotted in FIGS. 40 and 41, for 5.0 weight % GA nanogold (200 ppm) and for 5.0 weight % GA nanogold (200 ppm) with the addition of 1.0 weight % calcium chloride ($CaCl_2$)). As shown in FIGS. 40 and 41, the results without $CaCl_2$) have a peak of marginal satisfactory results while the plot for the process in the presence of the $CaCl_2$) likewise shows marginal satisfactory results (although minimal shifting occurred the peak is still not well defined) in the form of a normalized and dilution corrected charts (FIGS. 40 and 41).

Synthesis of Gum Arabic Encapsulated Gold Nanoparticles 10% GA 10.0 weight % of gum arabic (GA) (5.0 g/50 mL solution) is dissolved in de-ionized (DI) water (or distilled water) at room temperature with continuous stirring with a magnetic stirring bar. Gold salt ($HAuCl_4$) is then added to the GA solution as 0.5 weight % (0.0147M $HAuCl_4$), followed by a sodium hydroxide solution 1.0 weight % of NaOH (0.5 g/50 mL solution, often added to ~5-10 mL of deionized water first) while continuously stirred with a magnetic stirring bar.

After 24 hours of stirring, without heating, the product formed, GAAuNPs, are analyzed by optical absorbance measurements.

Figure 42:
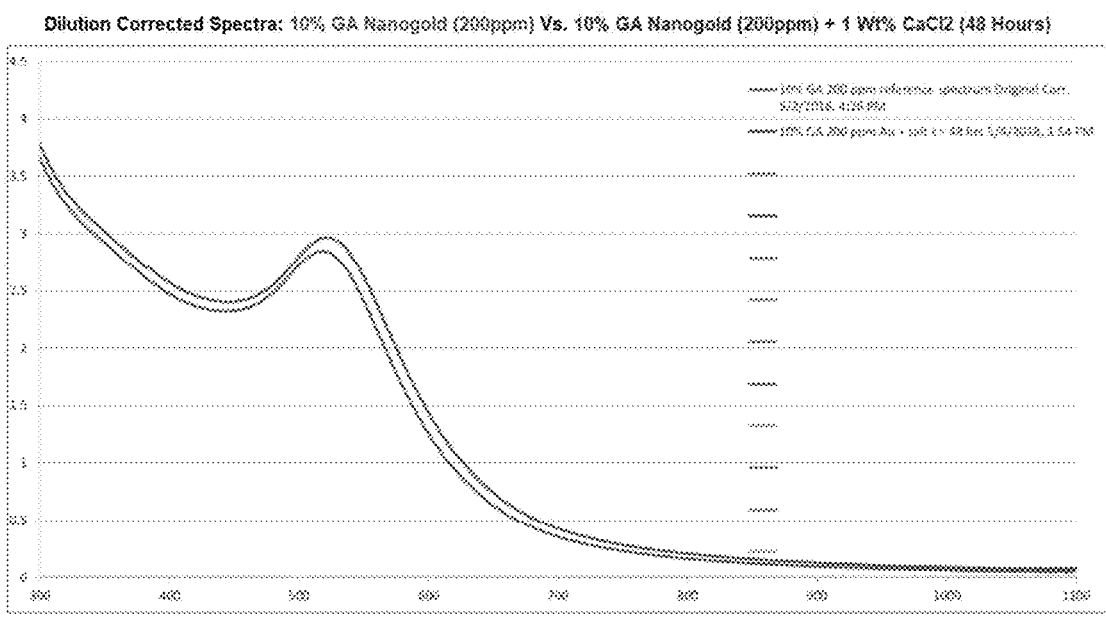
Figure 43:
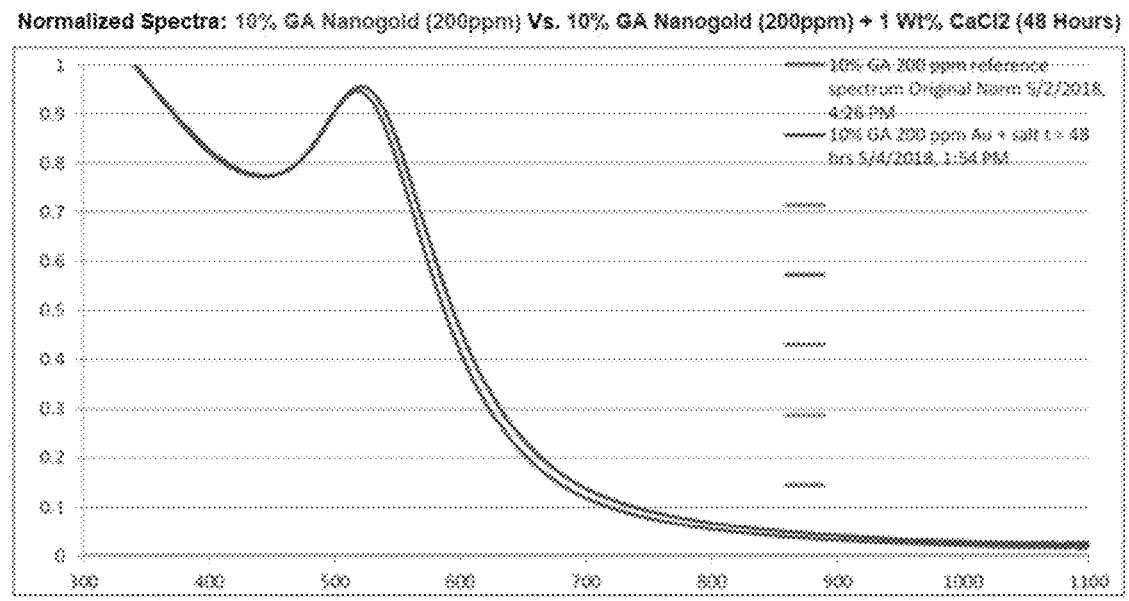

The results are plotted in FIGS. 42 and 43, for 10.0 weight % GA nanogold (200 ppm) and for 10.0 weight % GA nanogold (200 ppm) with the addition of 1.0 weight % calcium chloride ($CaCl_2$)). As shown in FIGS. 42 and 43, the results without $CaCl_2$) have a peak of satisfactory results while the plot for the process in the presence of the $CaCl_2$) shows results more satisfactory than prior, lower concentration experiments in the form of normalized and dilution corrected charts (FIGS. 42 and 43).

Synthesis of Gum Arabic Encapsulated Gold Nanoparticles 15% GA 15.0 weight % of gum arabic (GA) (7.5 g/50 mL solution) is dissolved in de-ionized (DI) water (or distilled water) at room temperature with continuous stirring with a magnetic stirring bar. Gold salt ($HAuCl_4$) is then added to the GA solution as 0.5 weight % (0.0147M $HAuCl_4$), followed by a sodium hydroxide solution 1.0 weight % of NaOH (0.5 g/50 mL solution, often added to ~5-10 mL of deionized water first) while continuously stirred with a magnetic stirring bar.

After 24 hours of stirring, without heating, the product formed, GAAuNPs, are analyzed by optical absorbance measurements.

Figure 44:
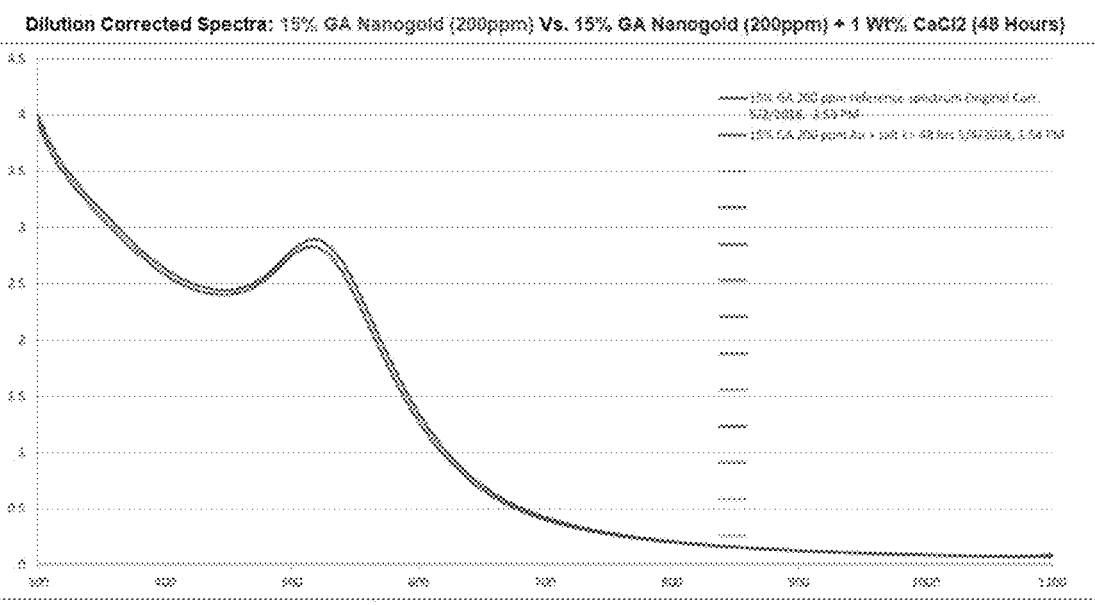
Figure 45:
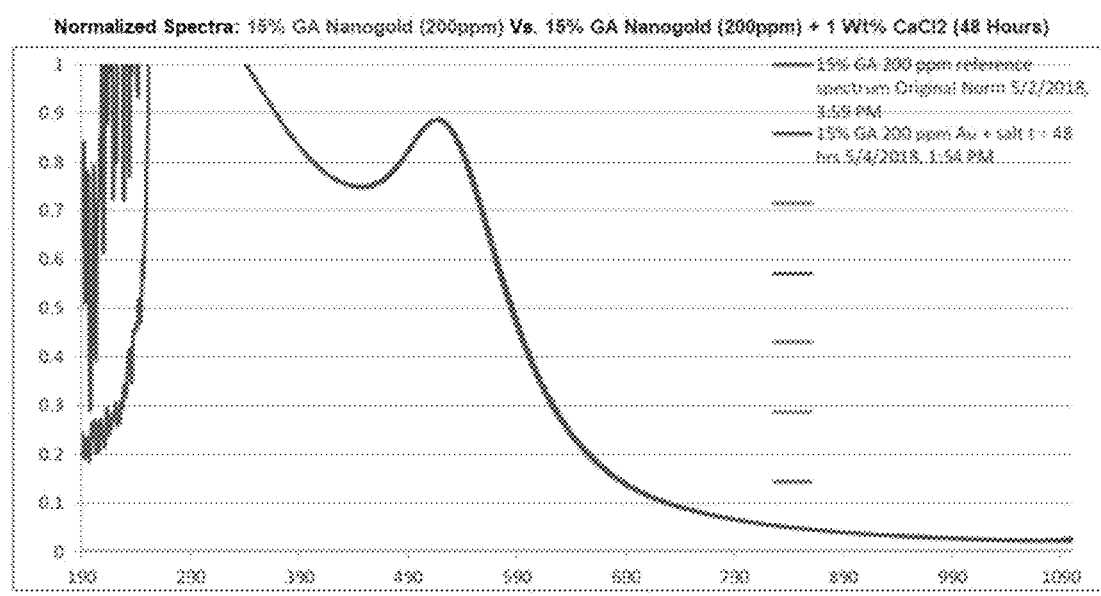
Figure 46:
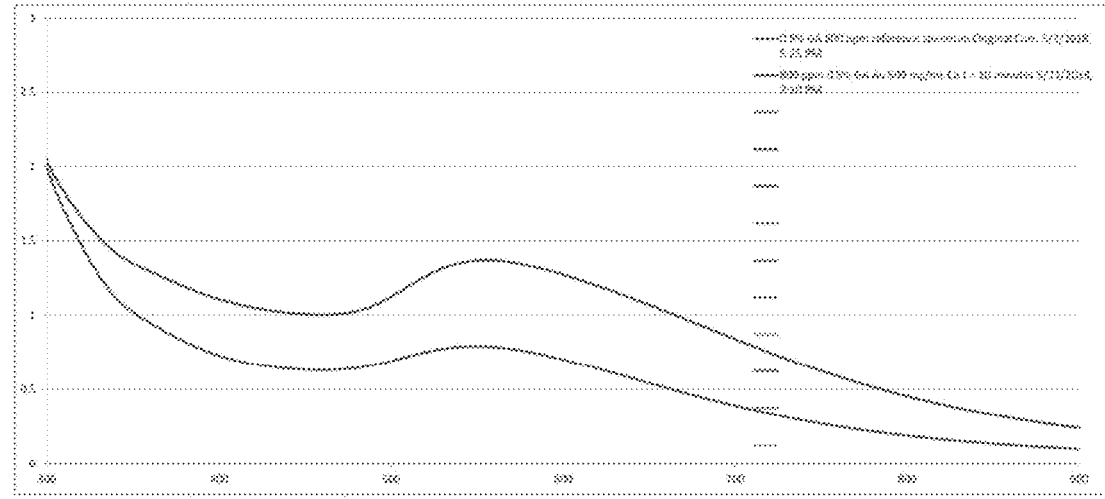
Figure 47:
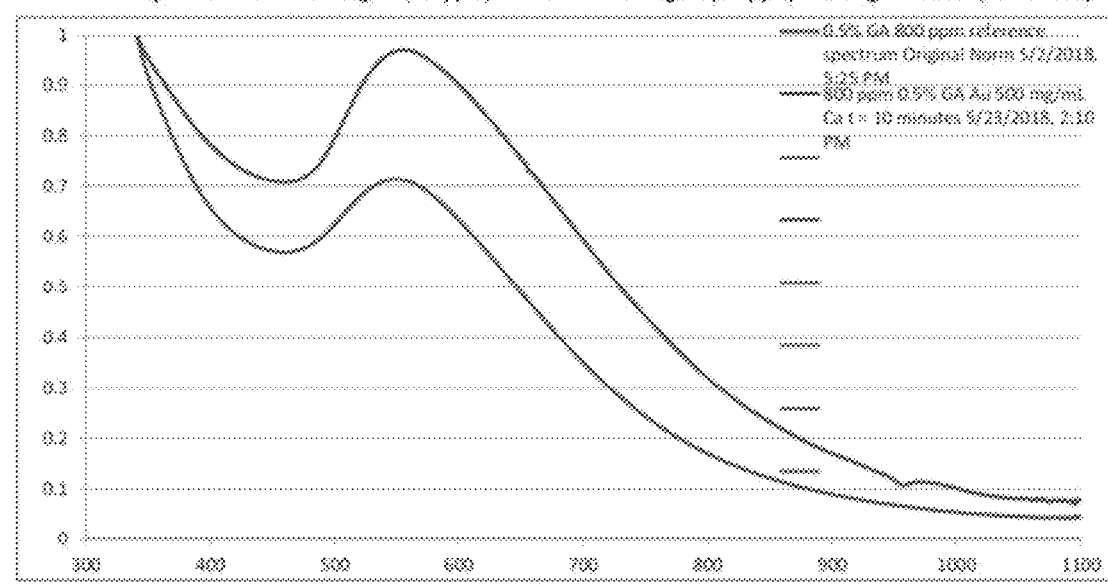
Figure 48:
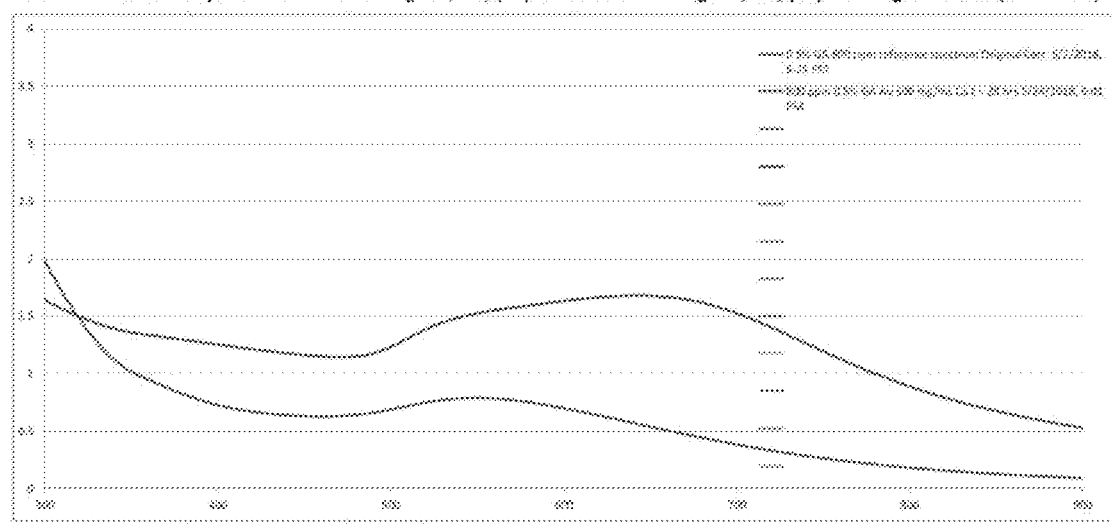
Figure 49:
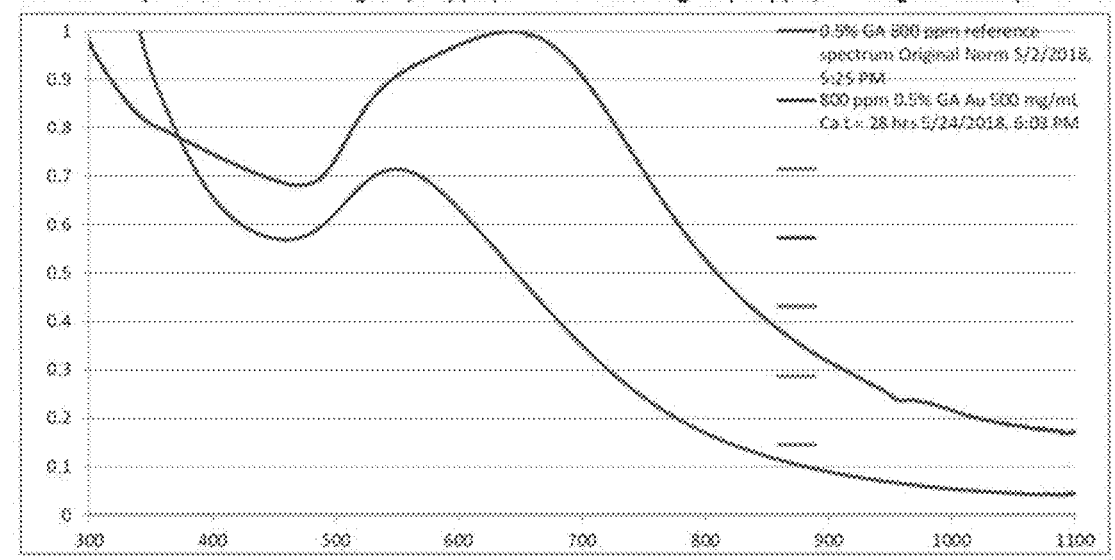
Figure 50:
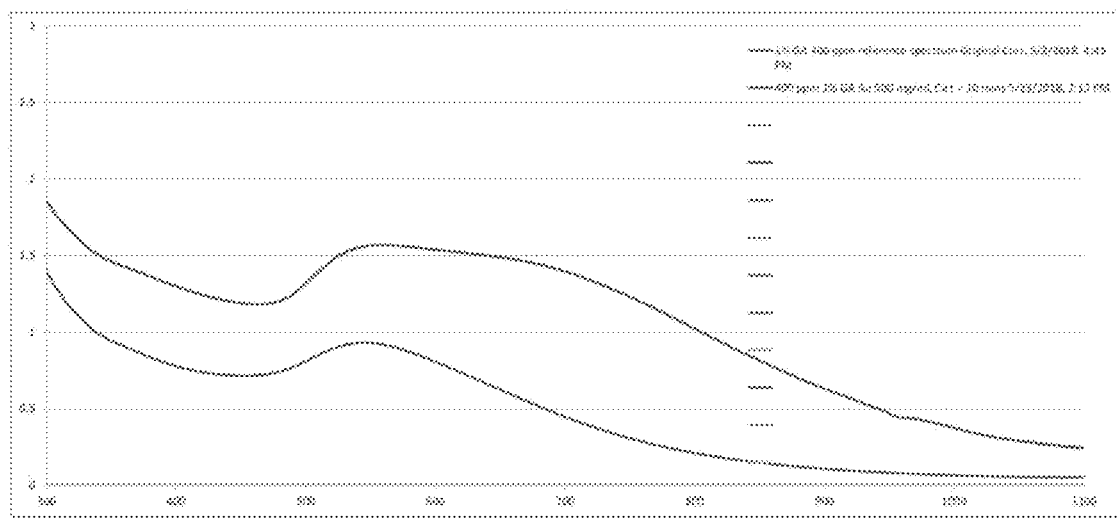
Figure 51:
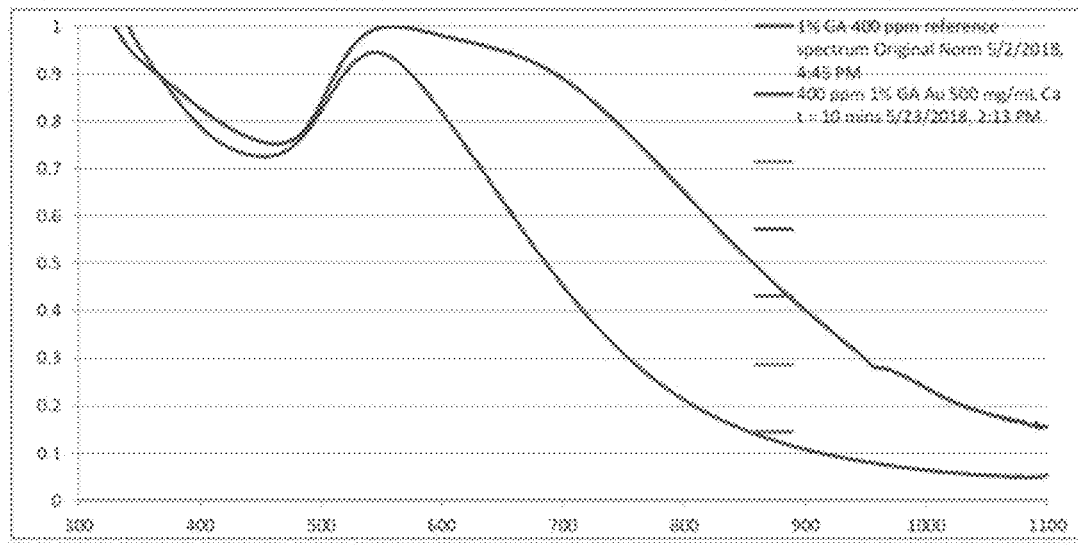
Figure 52:
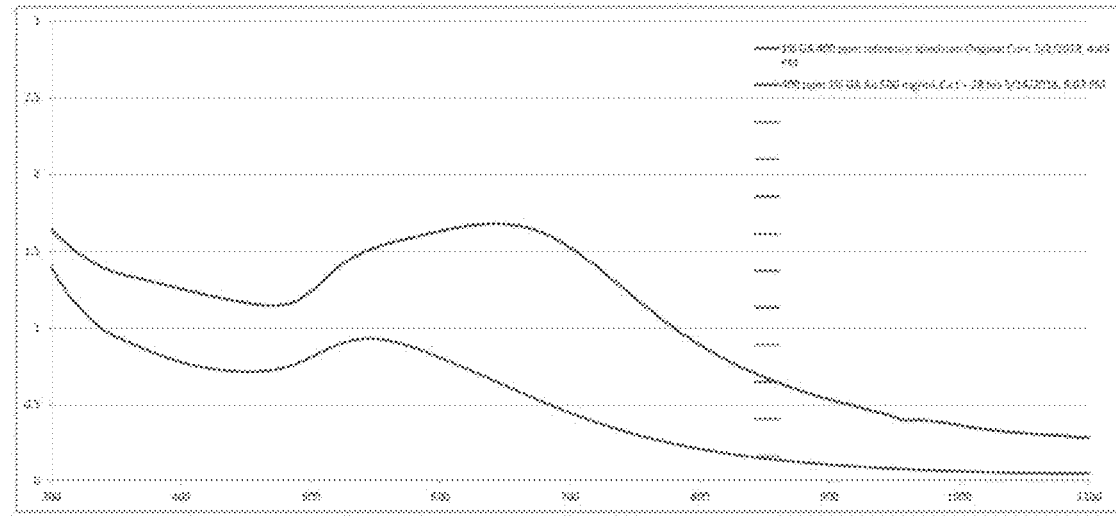
Figure 53:
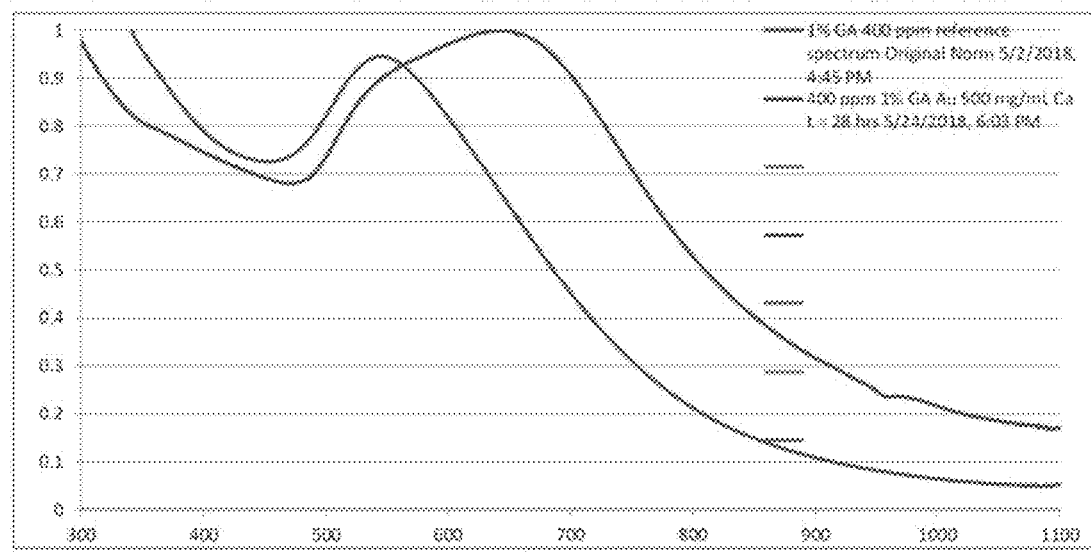
Figure 54:
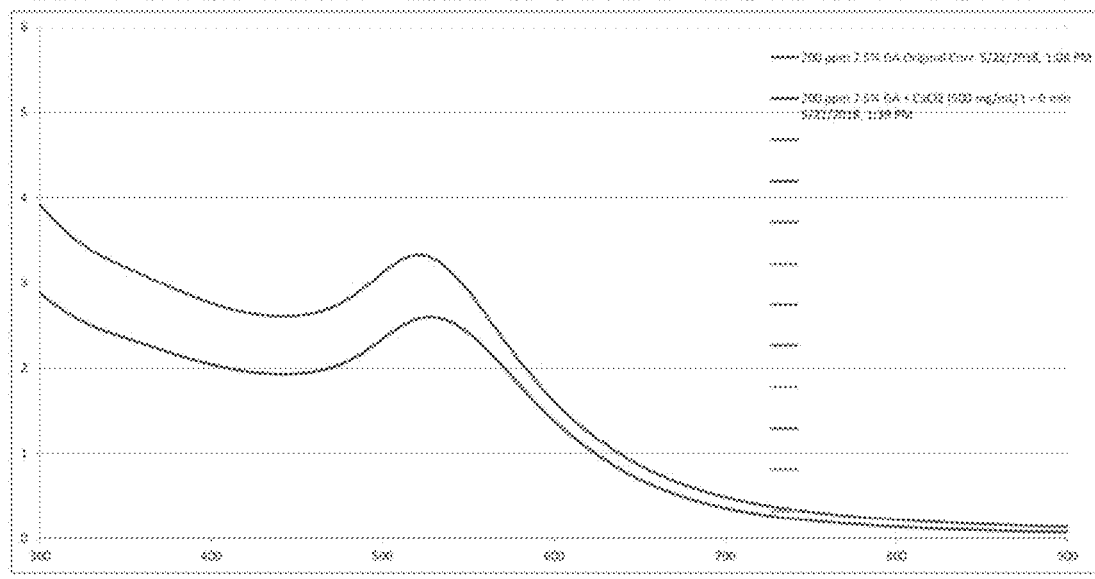
Figure 55:
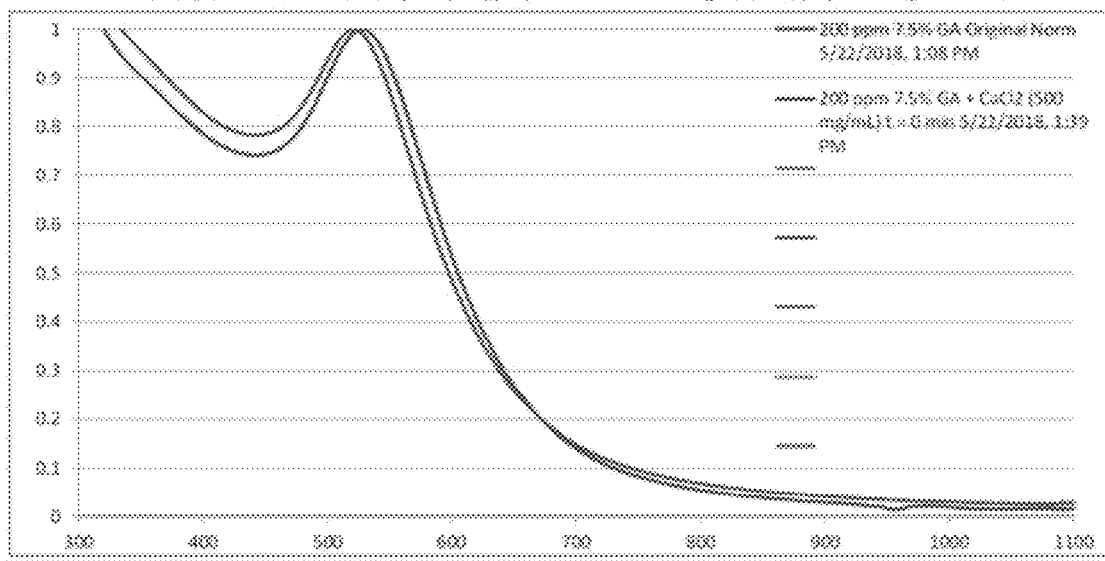
Figure 56:
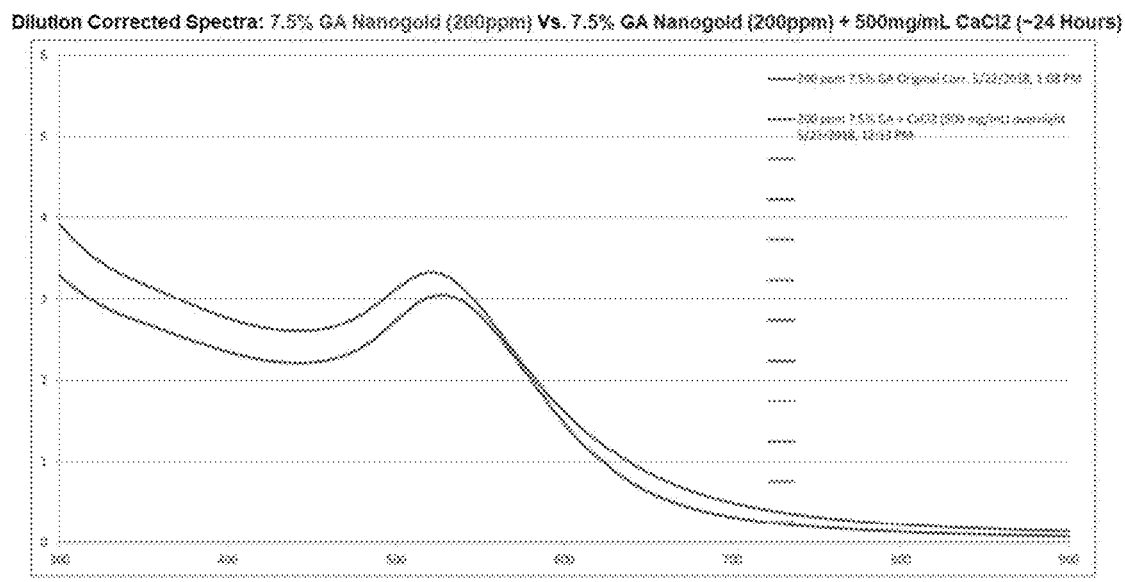
Figure 57:
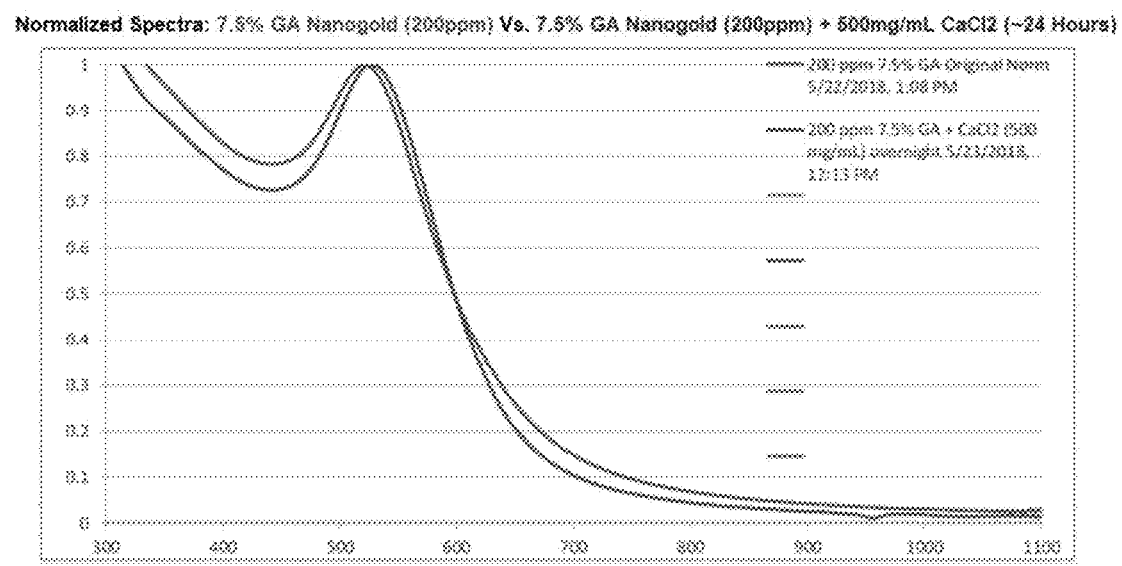

The results are plotted in FIGS. 44 and 45, for 15 weight % GA nanogold (200 ppm) and for 15 weight % GA nanogold (200 ppm) with the addition of 1.0 weight % calcium chloride ($CaCl_2$)). As shown in the plots in FIGS. 44 and 45, the results without $CaCl_2$) have a peak of satisfactory results while the plot for the process in the presence of the $CaCl_2$) shows satisfactory results even in the presence of $CaCl_2$) in the form of normalized and dilution corrected charts (FIGS. 44 and 45).

In order to show the limits of the stability of various gold nanoparticles, it was determined by the experimenter to test a higher $CaCl_2$) concentration to show more difference in the stability between synthesized gold nanoparticles with lower levels of GA and higher levels of GA. Therefore, a solution of 500 mg/mL of $CaCl_2$) was used on 3 different concentrations of gold nanoparticles comparable to prior art.

Synthesis of Gum Arabic Encapsulated Gold Nanoparticles—0.5% GA Extreme salt test 0.5 weight % of gum arabic (GA) (0.25 g/50 mL solution) is dissolved in de-ionized (DI) water (or distilled water) at room temperature with continuous stirring with a magnetic stirring bar. Gold salt ($HAuCl_4$) is then added to the GA solution as 0.5 weight % (0.0147 M $HAuCl_4$), followed by a sodium hydroxide solution 1.0 weight % of NaOH (0.5 g/50 mL solution, often added to ~5-10 mL of deionized water first) while being continuously stirred with a magnetic stirring bar.

After 24 hours of stirring, without heating, the product formed, GAAuNPs, are analyzed by optical absorbance measurements.

The results are plotted in FIGS. 46-49, for 0.5 weight % GA nanogold (800 ppm) and for 0.5 weight % GA nanogold (800 ppm) with the addition of 500 mg/mL calcium chloride ($CaCl_2$)). As shown in the plots in FIGS. 48-51, the results without $CaCl_2$) have a peak of unsatisfactory results while the plot for the process in the presence of the $CaCl_2$) also shows rather poor, unsatisfactory results in the form of a normalized and dilution corrected charts for initial measurements after the $CaCl_2$) was added (0-10 minutes) and after 24 hours of time. (FIGS. 46, 47, 48, and 49):

Representative proportions for nanogold with extreme calcium salt ($CaCl_2$)) concentrations are provided in Table 7.

Concentrations for nanogold extreme calcium salt experiments are provided in Table 8.

TABLE 8

NANOGOLD EXPERIMENTAL SAMPLES extreme calcium salt study 500 mg/mL $CaCl_2$:

| Sample: (GAAuNP Samples Derived from Synthesis in Table 4) | GA Nanogold (GAAuNPs) + H2O + 500 mg/mL $CaCl_2$ Extreme EXPERIMENTAL SALT TRIAL |
| --- | --- |
| GldGA-CAL(0.5) | 0.5% GA Sample (800 ppm) |
| GldGA-CAL(1) | 1% GA Sample (400 ppm) |
| GldGA-CAL(7.5) | 7.5% GA Sample (200 ppm) |

Nanogold baseline reference amounts are provided in Table 9.

TABLE 9

NANOGOLD BASELINE REFERENCE for extreme salt study:

| Sample: (GAAuNP Samples Derived from Synthesis in Table 4) | GA Nanogold (GAAuNPs) + H2O: BASELINE REFERENCE |
| --- | --- |
| GldGA(.5) | .5% GA Sample (800 ppm) |
| GldGA(1) | 1% GA Sample (400 ppm) |
| GldGA(7.5) | 7.5% GA Sample (200 ppm) |

Synthesis of Gum Arabic Encapsulated Gold Nanoparticles—1.0% GA Extreme Salt Test 1.0 weight % of gum arabic (GA) (0.5 g/50 mL solution) is dissolved in de-ionized (DI) water (or distilled water) at room temperature with continuous stirring with a magnetic stirring bar. Gold salt ($HAuCl_4$) is then added to the GA solution as 0.5 weight % (0.0147M $HAuCl_4$), followed by a sodium hydroxide solution 1.0 weight % of NaOH (0.5 g/50 mL solution, often added to ~5-10 mL of deionized water first) while being continuously stirred with a magnetic stirring bar.

TABLE 7

Synthesized Base GA Nanogold(GAAuNPs) for Nanogold Extreme Calcium Salt Samples:

| Sample: (GAAuNP Samples Derived from Synthesis in Table 4 and are repeated here) | Gold Salt ($HAuCl_4$)-(Wt %) | Gum Arabic (Wt %) | Ratio of Gum:Salt | Accelerator (NaOH Wt %) |
| --- | --- | --- | --- | --- |
| GldGA-BASE (0.5) | .5% (0.25 g or 0.0147M $HAuCl_4$) | 0.5% (0.25 g/50 mL) | 1:1 | 1% (0.5 g/50 mL) |
| GldGA-BASE (1) | 0.5% | 1% (0.5 g/50 mL) | 2:1 | 1% |
| GldGA-BASE (7.5) | 0.5% | 7.5% (3.75 g/50 mL) | 15:1 | 1% |

After 24 hours of stirring, without heating, the product formed, GAAuNPs, are analyzed by optical absorbance measurements.

The results are plotted in FIGS. 50, 51, 52, 53, for 1.0 weight % GA nanogold (400 ppm) and for 1 weight % GA nanogold (400 ppm) with the addition of 500 mg/mL calcium chloride ($CaCl_2$)). As shown in FIGS. 50-53s the results without $CaCl_2$) have a peak of unsatisfactory results while the plot for the process in the presence of the $CaCl_2$) also shows rather poor, unsatisfactory results in the form of a normalized and dilution corrected charts for initial measurements after the $CaCl_2$) was added (0-10 minutes) and after 24 hours of time. (FIGS. 50-53).

Synthesis of Gum Arabic Encapsulated Gold Nanoparticles—7.5% GA Extreme Salt Test 7.5 weight % of gum arabic (GA) (3.75 g/50 mL solution) is dissolved in de-ionized (DI) water (or distilled water) at room temperature with continuous stirring with a magnetic stirring bar. Gold salt ($HAuCl_4$) is then added to the GA solution as 0.5 weight % (0.0147M $HAuCl_4$), followed by a sodium hydroxide solution 1.0 weight % of NaOH (0.5 g/50 mL solution, often added to ~5-10 mL of deionized water first) while being continuously stirred with a magnetic stirring bar.

After 24 hours of stirring, without heating, the product formed, GAAuNPs, are analyzed by optical absorbance measurements.

The results are plotted in FIGS. 54-57 for 7.5 weight % GA nanogold (200 ppm) and for 1.0 weight % GA nanogold (200 ppm) with the addition of 500 mg/mL calcium chloride ($CaCl_2$)). As shown in FIGS. 54-57 the results without $CaCl_2$) have a peak show satisfactory results while the plot for the process in the presence of the $CaCl_2$) also shows mild shifting and satisfactory results in the form of a normalized and dilution corrected charts for initial measurements after the $CaCl_2$) was added (0-10 minutes) and after 24 hours of time. (FIGS. 54-57). This experiment demonstrates that even in extreme salt conditions that drastic improvements in salt stability were made by increasing the level of GA in the GAAuNPs synthesis process.

Synthesis of Gum Arabic Encapsulated Gold Nanoparticles—15% GA Xylitol/Calcium Acetate Testing 15 weight % of gum arabic (GA) (7.5 g/50 mL solution) is dissolved in de-ionized (DI) water (or distilled water) at room temperature with continuous stirring with a magnetic stirring bar. Gold salt ($HAuCl_4$) is then added to the GA solution as 0.5 weight % (0.0147M $HAuCl_4$), followed by a sodium hydroxide solution 1.0 weight % of NaOH (0.5 g/50 mL solution, often added to ~5-10 mL of deionized water first) while being continuously stirred with a magnetic stirring bar. After 24 hours of stirring, without heating, the product formed, GAAuNPs, are analyzed by optical absorbance measurements.

Figure 58:
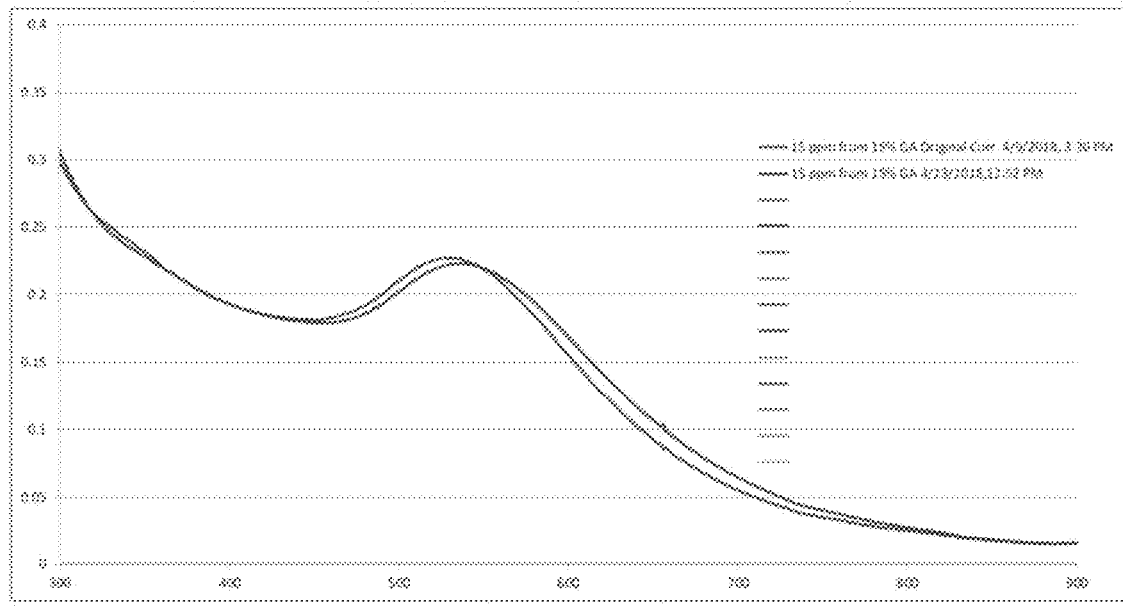
Figure 59:
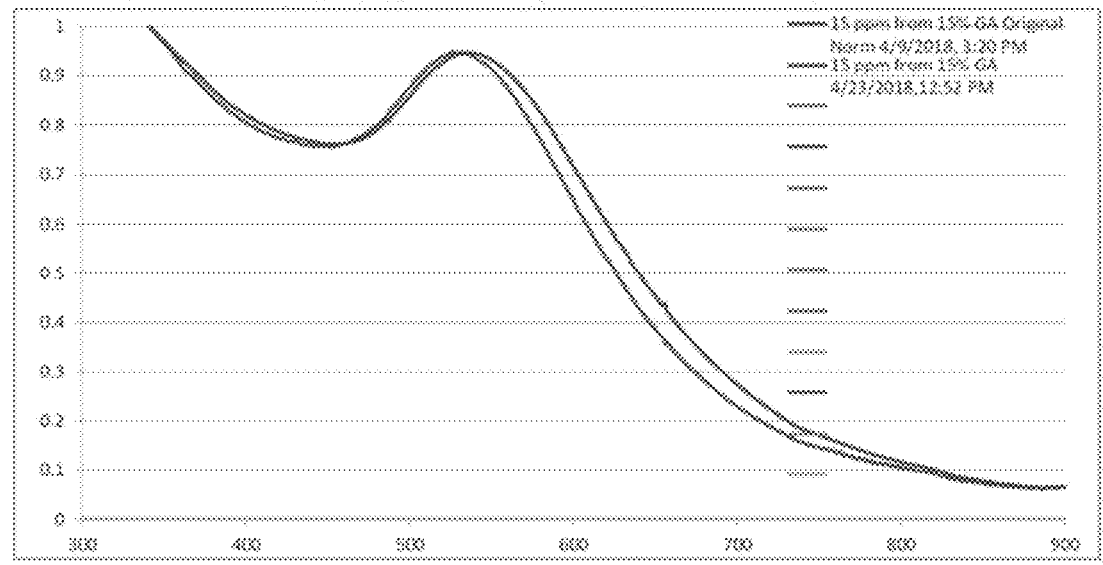
Figure 60:
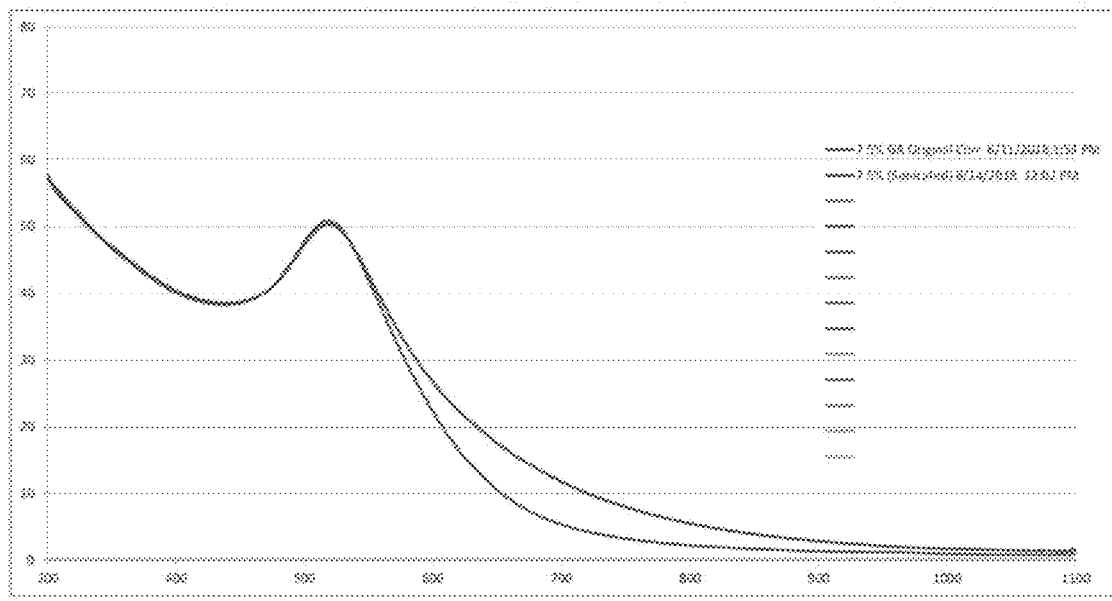
Figure 61:
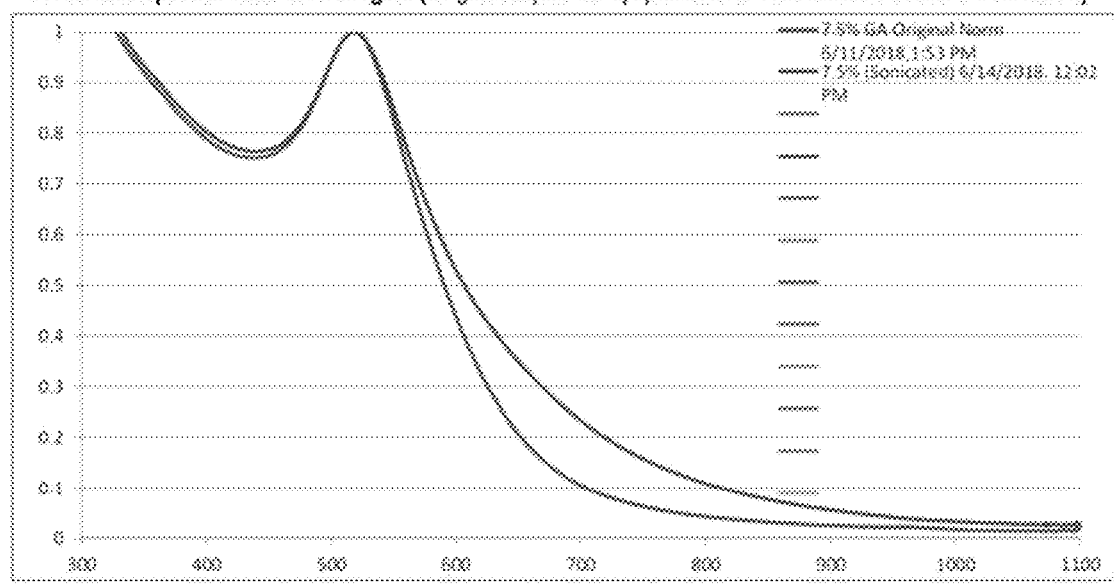
Figure 62:
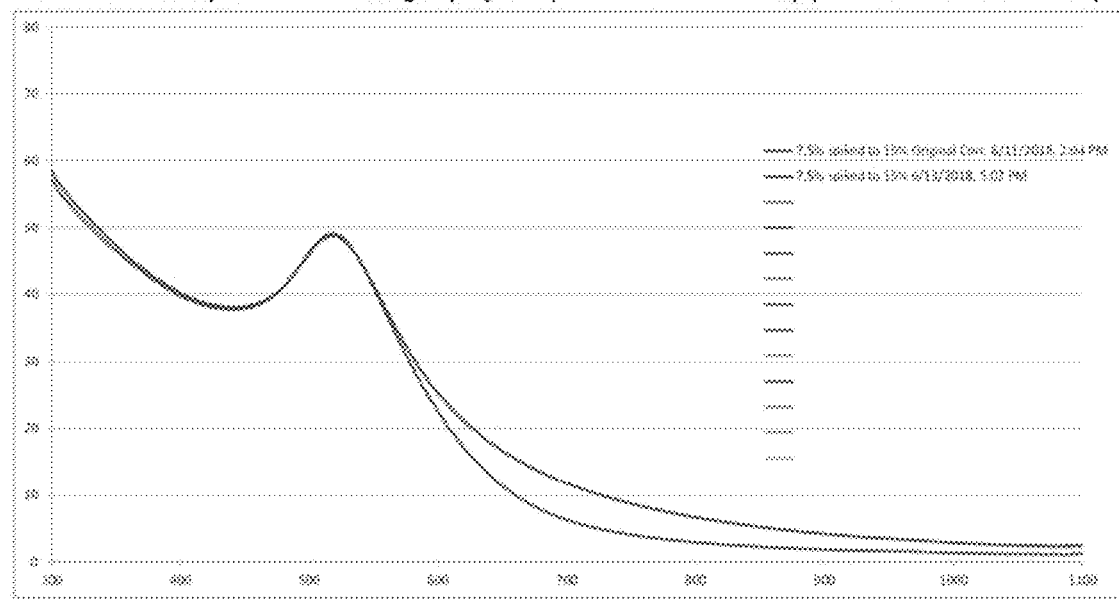
Figure 63:
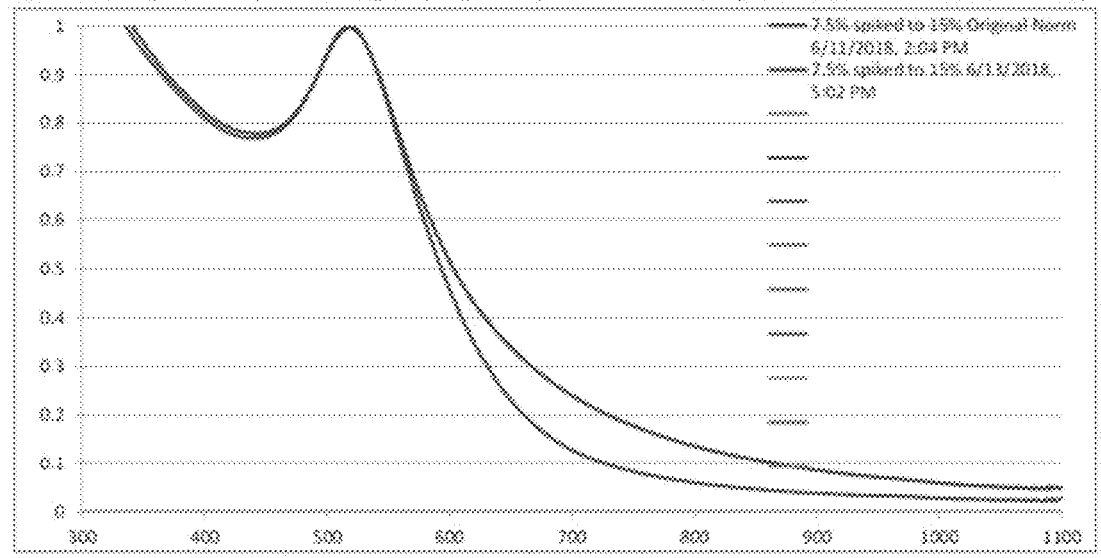
Figure 64:
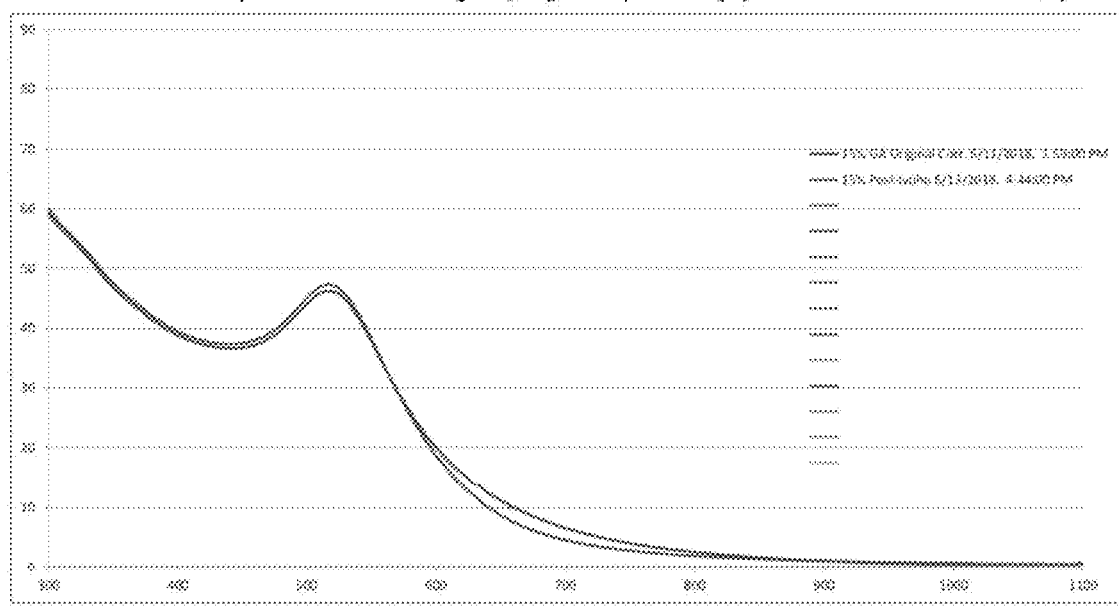

The results are plotted in FIGS. 58 and 59 for 15 weight % GA nanogold (15 ppm) and for 15 weight % GA nanogold (15 ppm) with the addition of 25 weight % xylitol and 0.9 weight % calcium acetate. As shown in FIGS. 58 and 59 the results show minimal shifting and satisfactory results in the form of a normalized and dilution corrected charts for initial measurements after the Ca—Ac and xylitol was added over a 2 week interval. (FIGS. 58 and 59):

Gum Arabic Encapsulated Gold Nanoparticles Synthesized with GA Stability after Lyophilization Varying weight % GA-"X" where X=7.5%, 7.5% spiked to 15.0%, or 15.0% of gum arabic (GA) (Where GA=3.75 g, 3.75 g+(3.75 g spiked), or 7.5 g per 50 mL solution respectively) is dissolved in de-ionized (DI) water (or distilled water) at room temperature with continuous stirring with a magnetic stirring bar. Gold salt ($HAuCl_4$) is then added to the GA solution as 0.5 weight % (0.0147M $HAuCl_4$), followed by a sodium hydroxide solution 1.0 weight % of NaOH (0.5 g/50 mL solution, often added to ~5-10 mL of deionized water first) while being continuously stirred with a magnetic stirring bar.

After 24 hours of stirring, without heating, the product formed, GAAuNPs, are analyzed by optical absorbance measurements.

The results are plotted in FIGS. 60-65, for 7.5 weight %, 7.5% (spiked to 15.0%) and 15.0 weight % GA synthesized nanogold. The results are satisfactory above 7.5 weight % GA and preferably 15 weight % GA, showing minimal changes even after lyophilization. 7.5 weight % results are, showing deviations from the original baseline synthesized nanogold product. Lower Wt % GA samples were sonicated but this did not improve the final result compared to 15% GA Lyophilization. This is shown in the form of a normalized and dilution corrected charts in which the powder is reconstituted into water and re-examined compared to the original sample. (FIGS. 60-65):

The experiments demonstrated that although the concentrations differ between silver and gold nanoparticle synthesis, an unexpected and striking effect occurred in the range of from about 12 weight % GA to about 15 weight % GA, often with at least a minimum of about 12 weight % GA starting when mixing the metal salt into the GA solution. Before these experiments, others had synthesized metal nanoparticles with concentrations of GA at a maximum level of about 2.5 weight % to about 5 weight %, often at about 1 weight %, which provided unsatisfactory results. The unsatisfactory results from prior methods included not being stable for a reasonable shelf life, not being stable in a high ionic strength environment (i.e., $CaCl_2$)), not easily rendered into monodisperse product, instability at high temperatures, and not producing a product that is sustainable over a wide pH range.

The methods described herein may be modified or altered to comprise more aspects, concurrently steps, simultaneous steps, or other variations.

It should be understood, of course, that the foregoing relates to exemplary embodiments of the invention and that modifications may be made without departing from the spirit and scope of the invention as set forth in the following claims. Furthermore, a method herein described may be performed in one or more sequences other than the sequence presented expressly herein.

Those of skill in the art would further appreciate that the various illustrative steps described in connection with the embodiments disclosed herein may be implemented with electronic hardware, computer software, or combinations of both. Some of the embodiments and implementations are described above in terms of functional components and various processing steps. However, it should be appreciated that such components may be realized by any number of hardware, software, and/or firmware components configured to perform the specified functions. Whether such functionality is implemented with hardware or software depends upon the particular application and design constraints imposed on the overall system. Skilled artisans may implement the described functionality in varying ways for each particular application, but such implementation decisions should not be interpreted as causing a departure from the scope of the present invention.

The word "exemplary" is used exclusively herein to mean "serving as an example, instance, or illustration." Any embodiment described herein as "exemplary" is not necessarily to be construed as preferred or advantageous over other embodiments.

In this document, relational terms such as first and second, and the like may be used solely to distinguish one entity or action from another entity or action without necessarily requiring or implying any actual such relationship or order between such entities or actions. Numerical ordinals such as "first," "second," "third," and such simply denote different singles of a plurality and do not imply any order or sequence unless specifically defined by the claim language. The sequence of the text in any of the claims does not imply that method steps must be performed in a temporal or logical order according to such sequence unless it is specifically defined by the language of the claim. The method steps may be interchanged in any order without departing from the scope of the invention as long as such an interchange does not contradict the claim language and is not logically nonsensical.

Furthermore, depending on the context, two elements may be connected to each other physically or in any other manner, through one or more additional elements.

While at least one exemplary embodiment has been presented in the foregoing detailed description, it should be appreciated that a vast number of variations exist. It should also be appreciated that the exemplary embodiments are only examples, and are not intended to limit the scope, applicability, or configuration of the invention in any way. Rather, the foregoing detailed description will provide those skilled in the art with a convenient road map for implementing the exemplary embodiments. It should be understood that various changes can be made in the function and arrangement of elements without departing from the scope of the invention as set forth in the appended claims and the legal equivalents thereof.

The invention claimed is:

1. A kit for treating patients with gum arabic encapsulated metal nanoparticles, comprising:
    an aqueous solution of the gum arabic, wherein the gum arabic is present at least at 12 weight percent in the base aqueous solution before directly coating metal nanoparticles with gum arabic; and
    metal nanoparticles directly coated with gum arabic.

2. The kit of claim 1 wherein the metal nanoparticles comprise silver.

3. The kit of claim 1 wherein the coated metal nanoparticles have a diameter of less than about 20 nm.

4. The kit of claim 1 wherein the coated metal nanoparticles have a diameter of greater than about 20 nm.

5. Metal nanoparticles stabilized with a material coating applied by using a solution comprising gum arabic in an aqueous solution wherein the base aqueous solution contains at least 12 weight percent gum arabic; wherein the metal nanoparticles consist essentially of metal cores;
    and wherein the metal cores are in the size range of 5-10 nm.

6. The metal nanoparticles of claim 5, wherein the metal nanoparticles are monodisperse.

7. The metal nanoparticles of claim 6 wherein the metal nanoparticles comprise silver.

\* \* \* \* \*